United States Patent
Rii et al.

(10) Patent No.: US 9,713,636 B2
(45) Date of Patent: Jul. 25, 2017

(54) NUCLEIC ACID/POLYSACCHARIDE COMPLEX

(75) Inventors: Ko Rii, Chofu (JP); Kazuo Sakurai, Himeji (JP); Masakazu Kobayashi, Kawanishi (JP); Hironori Ando, Nishitokyo (JP); Sadaharu Higuchi, Nishitokyo (JP); Shiro Takahara, Ikeda (JP)

(73) Assignee: NAPAJEN PHARMA, INC., Burlingame, CA (US)

( * ) Notice: Subject to any disclaimer, the term of this patent is extended or adjusted under 35 U.S.C. 154(b) by 0 days.

(21) Appl. No.: 14/001,694

(22) PCT Filed: Feb. 15, 2012

(86) PCT No.: PCT/JP2012/053583
§ 371 (c)(1),
(2), (4) Date: Oct. 28, 2013

(87) PCT Pub. No.: WO2012/117855
PCT Pub. Date: Sep. 7, 2012

(65) Prior Publication Data
US 2014/0128448 A1    May 8, 2014

(30) Foreign Application Priority Data

Feb. 28, 2011 (JP) .................................. 2011-043310
Aug. 10, 2011 (WO) .................. PCT/JP2011/068265

(51) Int. Cl.
| | | |
|---|---|---|
| A61K 31/70 | (2006.01) |
| C07H 21/02 | (2006.01) |
| C07H 21/04 | (2006.01) |
| A61K 39/00 | (2006.01) |
| A61K 31/7105 | (2006.01) |
| A61K 31/716 | (2006.01) |
| C12N 15/11 | (2006.01) |
| C12N 15/113 | (2010.01) |
| C12N 5/00 | (2006.01) |

(52) U.S. Cl.
CPC ...... A61K 39/0013 (2013.01); A61K 31/7105 (2013.01); A61K 31/716 (2013.01); C12N 15/111 (2013.01); C12N 15/113 (2013.01); C12N 15/1138 (2013.01); A61K 2039/57 (2013.01); C12N 2310/315 (2013.01); C12N 2320/32 (2013.01); C12N 2320/50 (2013.01)

(58) Field of Classification Search
None
See application file for complete search history.

(56) References Cited

U.S. PATENT DOCUMENTS

| 7,521,433 B2 | 4/2009 | Kimura et al. |
| 8,017,742 B2 | 9/2011 | Sakurai et al. |
| 2005/0281815 A1* | 12/2005 | Eshel ............... C07K 14/70578 424/144.1 |
| 2006/0216343 A1 | 9/2006 | Panzner et al. |
| 2007/0009517 A1* | 1/2007 | De Boer ............... A61K 31/00 424/144.1 |
| 2007/0098718 A1 | 5/2007 | Long et al. |
| 2011/0111501 A1* | 5/2011 | Kubo et al. .................. 435/375 |

FOREIGN PATENT DOCUMENTS

| EP | 2 226 384 A1 | 9/2010 |
| WO | WO2005044294 * | 5/2005 |
| WO | WO 2007/058323 | 5/2007 |
| WO | WO 2009/078470 | 6/2009 |

OTHER PUBLICATIONS

Higuchi et al., Transplantation vol. 94 Supp. 10S, p. 1129, Jul. 15, 2012.*
Suzuki, Motohiko et al., "Regulation of allergic response by short interfering RNA", Journal of Japan Society of Immunology & Allergology in Otolaryngology (JJIAO), vol. 28, No. 3, pp. 223-228. (2010) (Abstract only).
Matsumoto, et al., "Chemically modified polysaccharide schizophyllan for antisense oligonucleotides delivery to enhance the cellular uptake efficiency," Biochimica et Biophysica Acta (BBA)-General Subjects, vol. 1670, No. 2, pp. 91-104 (2004).
Karinaga, et al., "Galactose-PEG dual conjugation of β-( 1→3)-d-glucan. schizophyllan for antisense oligonucleotides delivery to enhance the cellular uptake," Biomaterials, vol. 27, No. 8, pp. 1626-1635 (2006).
Karinaga, et al., "PEG-appended β-(1->3)-d-glucan schizophyllan to deliver antisense-oligonucleotides with avoiding lysosomal degradation." Biomaterials, vol. 26, No. 23, pp. 4866-4873 (2005).
Mizu, et al., "Antisense oligonucleotides bound in the polysaccharide complex and the enhanced antisense effect due to the low hydrolysis," Biomaterials vol. 25, No. 15, pp. 3117-3123 (2004).
Mizu, et al. "Enhancement of the Antisense Effect of Polysaccharide-Polynucleotide Complexes by Preventing the Antisense Oligonucleotide from Binding to the Proteins in the Culture Medium", Bull. Chem. Soc. Japan., 2004, vol. 77, pp. 1101-1110.
Suzuki, et al. "A novel allergen-specific therapy for allergy using CD40-silenced dendritic cells" J. Allergy Clin. Immunol., 2010, vol. 58, No. 2, pp. 5018-5019.
Mochizuki, et al. "A novel polysaccharide/polynucleotide complex and its application to bio-functional DNA delivery systems" Polymer Journal, 2009, vol. 41, No. 5, pp. 343-353.
Mochizuki, et al. "Development of nucleic acid delivery system for targeting the antigen presenting cells" Polymer Preprints, 2009, vol. 58, No. 1, pp. 5018-5019.
Ikeda, et al. "Blocking effect of anti-Dectin-I antibodies on the anti-tumor activity of 1,3-beta-glucan and the binding of Dectin-I to 1,3-beta-glucan" Biol. Pharm. Bull., 2007, vol. 30, No. 8, pp. 1384-1389.
Mochizuki, et al. "Development of nucleic acid delivery system for targeting the antigen presenting cells" Polymer Preprints, 2009, vol. 58, No. 1, pp. 1175.

(Continued)

Primary Examiner — Sean McGarry
(74) Attorney, Agent, or Firm — Fay Sharpe LLP

(57) ABSTRACT

A highly stable nucleic acid-polysaccharide complex of an siRNA and schizophyllan is formed by adding polydeoxyadenine in which at least part of the phosphodiester link portion is phosphorothioated to an siRNA and allowing the siRNA and schizophyllan to form a complex.

4 Claims, 9 Drawing Sheets

(56) References Cited

OTHER PUBLICATIONS

Torras, et al., "Pre-Transplant Intra-Graft Silencing of CD40 Switches the Rejection Pattern from Humoral to Cellular and Induces Accommodation of the Graft," Histocompatibility and Immunogenetics, Session P119-III, Abstract #1326, p. 419 (2010) Abstract Only.
Ritprajak, et al., "Regulation of immune responses by intervention of co-signals expressed on dendric cells," Experimental Medicine, vol. 26, No. 20, pp. 82(3204)-88(3210) (2008). (Partial English translation).
Japanese Office Action for JP App. No. 2013-502238 mailed Sep. 13, 2016.

\* cited by examiner

NUCLEIC ACID/POLYSACCHARIDE COMPLEX

This application claims priority to and the benefit of PCT International Application Number PCT/JP2012/053583, filed on Feb. 15, 2012, JP 2011-043310, filed Feb. 28, 2011, and PCT/JP2011/068265, filed Aug. 10, 2011, the disclosures of which are incorporated herein by reference in their entireties.

BACKGROUND

Technical Field

The present invention relates to a highly stable nucleic acid-polysaccharide complex of an siRNA and schizophyllan. Also, the present invention relates to a method for controlling the function of a Dectin-1 expressing cell such as a dendritic cell and obtaining an effective therapeutic effect by inhibiting expression of a target gene using the nucleic acid-polysaccharide complex, and to a drug for use in the method. Moreover, the present invention relates to a method for immunomodulation and a drug for use therein. In particular, the present invention relates to a drug or the like for use in the suppression of rejection occurring in organ transplantation and for use in the treatment of allergies and autoimmune diseases, using an siRNA against a costimulatory factor and a highly stable nucleic acid-polysaccharide complex of schizophyllan.

Background Art

RNA interference (RNAi) discovered in 1998 has markedly superior efficacy and persistence to conventional antisense methods and is a breakthrough gene expression inhibitory method, and therefore there has been a hope for its pharmaceutical applications. However, a double strand RNA (i.e., siRNA) that shows an RNAi activity is often decomposed during the process from administration to uptake into a target cell or decomposed in a cell, and it has been difficult to form a RISC complex, i.e., its active substance, in a cell. Accordingly, even though it is a superior gene expression inhibitory method, a sufficient effect is not obtainable, and therefore a pharmaceutical product that uses an siRNA is not yet available.

Unmodified siRNAs are decomposed by nuclease that is present in, for example, blood, and few unmodified siRNAs demonstrate an RNAi effect in a target cell. Accordingly, various chemical modifications to give nuclease resistance have been performed on siRNAs. Nevertheless, a high dosage is necessary for effective introduction into a cell. Also, it is known that because administration of a double strand nucleotide into a living body in a high dosage enhances a natural immunoreaction, an unintended effect, i.e., immunostimulatory reaction, appears. Accordingly, a delivery technique to specifically introduce an siRNA into a target cell is necessary. For siRNA delivery techniques, techniques to embed an siRNA, such as liposomes and macromolecular nanomicelles, have been developed. However, in terms of target tropism, these delivery techniques are still within the meaning of passive targeting, and in order to overcome this shortcoming, a procedure for imparting, for example, a molecule that binds to the target cell to an siRNA drug is needed.

With such conventional art as background, a demand exists for positive targeting and a delivery technique for an siRNA that shows an RNAi activity significantly within the target cell. Accordingly, as a delivery method of an siRNA to a dendritic cell, a complex of schizophyllan and a polydeoxyadenine-added siRNA has been proposed (see WO 2009/078470). However, it is not necessarily possible to obtain a satisfactory therapeutic effect with the technique of WO 2009/078470.

On the other hand, it has been reported so far that phosphorothioated polydeoxyadenine can form a stable complex with schizophyllan (see Bull. Chem. Soc. Jpn., 77, 1101-1110 (2004)). However, it is thought that a complex of schizophyllan and an siRNA to which phosphorothioated polydeoxyadenine is added is not possible to exhibit an effective RNA interference effect for the following reasons. In the complex of schizophyllan and a polydeoxyadenine-added siRNA, the complexing portion between polydeoxyadenine and schizophyllan serves as a steric hindrance in the formation of a RISC complex. Therefore, in the complex of schizophyllan and a polydeoxyadenine-added siRNA, the portion where the complex with schizophyllan is formed needs to be removed before forming a RISC complex in a cell, but phosphorothioated polydeoxyadenine and schizophyllan have markedly high stability, thus being not easily removable. In addition, because phosphorothioated polydeoxyadenine is unlikely to be enzymatically resolved, it is difficult to remove the portion where a complex is formed between schizophyllan and an siRNA to which phosphorothioated polydeoxyadenine is added (in particular, a 21 mer type siRNA that is not affected by the action of Dicer). Therefore, it is thought that with regard to the complex of schizophyllan and an siRNA to which phosphorothioated polydeoxyadenine is added (in particular, a 21 mer type siRNA), it is not possible to separate the phosphorothioated polydeoxyadenine and schizophyllan from the siRNA in a cell, thus making it difficult to form a RISC complex.

Therefore, currently, it is thought that a complex of schizophyllan and an siRNA to which phosphorothioated polydeoxyadenine is added (in particular, a 21 mer type siRNA) is not usable from the technical viewpoint of effectively exhibiting an RNA interference effect.

SUMMARY OF INVENTION

Technical Problem

A primary object of the present invention is to provide a highly stable nucleic acid-polysaccharide complex of an siRNA and schizophyllan; a method for controlling the function of a Dectin-1 expressing cell such as a dendritic cell and obtaining an excellent therapeutic effect by inhibiting expression of a target gene using the nucleic acid-polysaccharide complex; and a drug for use in the method. Moreover, another primary object of the present invention is to provide a method for modulating an immune function and a drug for use therein. Furthermore, another primary object of the present invention is to provide a drug for use in the suppression of rejection occurring in organ transplantation.

Solution to Problem

Having conducted diligent research to solve the foregoing problems, the inventors found that, surprisingly, in the case where polydeoxyadenine in which at least part of the phosphodiester link portion is phosphorothioated is added to an siRNA, and is subjected to complex formation with schizophyllan, a complex is obtained that has superior stability, modulates the function of a cell that expresses Dectin-1, which specifically recognizes schizophyllan, when the complex is delivered to the cell, and gives a desired therapeutic effect. Moreover, the inventors also found that a nucleic acid-polysaccharide complex prepared by adding the polydeoxyadenine to an siRNA that is directed to a gene that affects the in vivo function for which the Dectin-1 expressing cell is responsible and subjecting the polydeoxyadenine to complex formation with schizophyllan can modulate in vivo immunity and can preventively or therapeutically induce immunosuppression. Actually, the inventors found that a very excellent effect is shown in cardiac transplantation models using an siRNA against CD40. Moreover, the inventors also found that a nucleic acid-polysaccharide complex in which schizophyllan and a 21 mer type siRNA that has a sense strand to which phosphorothioated polydeoxyadenine is added are complexed allows the antisense strand to be incorporated into a RISC complex, thus making it possible to effectively exhibit an RNA interference effect. Based on these findings, the inventors conducted further research and arrived at the present invention.

The present invention provides, for example, a nucleic acid-polysaccharide complex and a method for producing the nucleic acid-polysaccharide complex as follows.

Item 1. A pharmaceutical preparation for suppressing rejection occurring in transplantation therapy, comprising a nucleic acid-polysaccharide complex of schizophyllan and a polynucleotide containing an siRNA to which polydeoxyadenine is added, against a costimulatory factor.

Item 2. The pharmaceutical preparation according to Item 1, wherein the siRNA is a 21mer type, and the polynucleotide contains polydeoxyadenine that has phosphodiester links at least partially phosphorothioated and that is added to a sense strand of the siRNA.

Item 3. The pharmaceutical preparation according to Item 1 or 2, wherein at least 50% of the phosphodiester links of the polydeoxyadenine are phosphorothioated.

Item 4. The pharmaceutical preparation according to any one of Items 1 to 3, wherein the costimulatory factor is that expressed in a Dectin-1 expressing cell.

Item 5. The pharmaceutical preparation according to any one of Items 1 to 4, wherein the costimulatory factor is any one of CD40, B7.1 and B7.2.

Item 6. The pharmaceutical preparation according to any one of Items 1 to 5, wherein the costimulatory factor is CD40.

Item 7. The pharmaceutical preparation according to any one of Items 1 to 6, wherein the transplantation therapy is kidney transplantation, heart transplantation, lung transplantation, bone marrow transplantation, skin transplantation, or corneal transplantation.

Item 8. A method for suppressing rejection occurring in transplantation therapy, comprising the step of administering a nucleic acid-polysaccharide complex of schizophyllan and a polynucleotide containing an siRNA to which polydeoxyadenine is added, against a costimulatory factor, to an animal in need of treatment or prophylaxis of resistance or rejection to a transplanted organ or tissue.

Item 9. Use of a nucleic acid-polysaccharide complex of schizophyllan and a polynucleotide containing an siRNA to which polydeoxyadenine is added, against a costimulatory factor, for the manufacture of a pharmaceutical agent for suppressing rejection occurring in transplantation therapy.

Item 10. A nucleic acid-polysaccharide complex of schizophyllan and a polynucleotide in which polydeoxyadenine having phosphodiester links that are at least partially phosphorothioated is added to an siRNA that is directed to a target gene.

Item 11. The nucleic acid-polysaccharide complex according to Item 10, wherein the siRNA is a 21 mer type, and the polynucleotide in which polydeoxyadenine having phosphodiester links that are at least partially phosphorothioated is added to a sense strand of the siRNA is added.

Item 12. The nucleic acid-polysaccharide complex according to Item 10 or 11, wherein the polydeoxyadenine has 30 to 50 nucleotides.

Item 13. The nucleic acid-polysaccharide complex according to any of Items 10 to 12, wherein at least 50% of the phosphodiester links of the polydeoxyadenine are phosphorothioated.

Item 14. The nucleic acid-polysaccharide complex according to any of Items 10 to 13, wherein the target gene is a gene expressed in a Dectin-1 expressing cell.

Item 15. The nucleic acid-polysaccharide complex according to any of Items 10 to 14, wherein the target gene is a costimulatory factor expressed in a Dectin-1 expressing cell.

Item 16. The nucleic acid-polysaccharide complex according to Item 15, wherein the costimulatory factor is a CD40 gene.

Item 17. A pharmaceutical composition containing a nucleic acid-polysaccharide complex of any of Items 10 to 16.

Item 18. A function modulator for a Dectin-1 expressing cell, containing a nucleic acid-polysaccharide complex of any of Items 10 to 16.

Item 19. The function modulator according to Item 18, wherein a function of the Dectin-1 expressing cell is an immunomodulatory function.

Item 20. An immunomodulator containing a nucleic acid-polysaccharide complex of any of Items 10 to 16.

Item 21. A method for modulating a function of a Dectin-1 expressing cell, including the step of bringing a nucleic acid-polysaccharide complex of schizophyllan and polynucleotide in which polydeoxyadenine having phosphodiester links that are at least partially phosphorothioated is added to an siRNA that is directed to a gene that affects an in vivo function for which a Dectin-1 expressing cell is responsible into contact with a cell that expresses Dectin-1.

Item 22. The method according to Item 21, wherein function modulation for the Dectin-1 expressing cell is immunomodulation.

Item 23. A method for modulating an immune function, including administering a nucleic acid-polysaccharide complex of schizophyllan and polynucleotide in which polydeoxyadenine having phosphodiester links that are at least partially phosphorothioated is added to an siRNA that is directed to a gene that affects an in vivo function for which a Dectin-1 expressing cell is responsible to an animal in need of immune function modulation.

Item 24. Use of a nucleic acid-polysaccharide complex of schizophyllan and polynucleotide in which polydeoxyadenine having phosphodiester links that are at least partially phosphorothioated is added to an siRNA that is directed to a gene that affects an in vivo function for which a Dectin-1 expressing cell is responsible for the manufacture of an immune function modulator.

Effect of Invention

According to the present invention, an RNAi activity can be induced by effectively introducing an siRNA into a target cell, and a disease relevant to the target cell can be treated by modulating the function of the target cell. Moreover, it is also possible to provide a treatment method that is based on the induction of immunosuppression with a low-dose siRNA drug by taking advantage of the nucleic acid-polysaccharide complex of the present invention. Particularly, it is possible to effectively suppress rejection occurring in transplantation therapy by using the nucleic acid-polysaccharide complex of the present invention.

DESCRIPTION OF EMBODIMENTS

Figure 1:
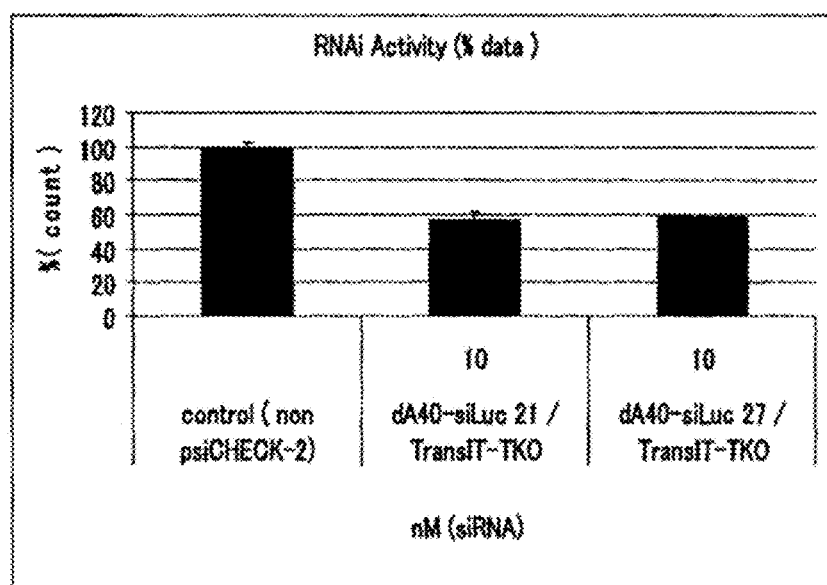
FIG. 1 is a chart showing the results of Example 4, or that is, an siRNA to which S-modified poly(dA) is linked can produce an RNA interference effect without being cleaved by Dicer.

1. Nucleic Acid-Polysaccharide Complex Containing Schizophyllan and siRNA Added to Polydeoxyadenine that May be Phosphorothioated, and Applications Thereof With regard to the nucleic acid-polysaccharide complex of the present invention, a polydeoxyadenine tail is added to at least one terminal of a sense strand or antisense strand that constitutes an siRNA directed to a target gene, and a triple helix is formed by one strand of polydeoxyadenine and two strands of schizophyllan. In the present invention, at least part of the phosphodiester links in the polydeoxyadenine tail may be phosphorothioated.

The complex of the present invention contains an siRNA composed of a base sequence that matches the target sequence in the target gene as a portion responsible for an RNA interference effect. Here, the siRNA may be a sequence that 100% matches the target sequence, or one or several bases may be replaced or added as long as the desired RNA interference effect is obtained.

Here, the target gene is a gene that is a subject of inhibition of gene expression by an RNA interference effect. With regard to the nucleic acid-polysaccharide complex of the present invention, the target gene is not particularly limited, and can be suitably selected based on the application of the nucleic acid-polysaccharide complex.

The target gene in the present invention is not particularly limited, but from the viewpoint of use in pharmaceutical applications, a gene that is involved in a disease state and inhibition of its expression is hoped is suitable. Specific examples of the target gene include (a) a gene that encodes a factor involved in the onset of a disease state or aggravation of a symptom while excessively producing its transcription product via an external stimulus or the like and (b) a target gene that has a mutated site and encodes a factor that is directly involved in the onset of a disease while producing its transcription product.

Examples of the target gene include genes that encode factors that induce inflammation, such as cytokines such as TNFα, interleukin, and MIF.

Genes that encode factors that determine ON/OFF of intracellular activities are also encompassed within the target gene (a). Examples of such genes include protein kinases (for example, Raf, MEK, and Jaks), transcription factors (for example, Stats), and the like.

Moreover, the target gene (a) encompasses a target gene that encodes a cell surface receptor and also a target gene that encodes a factor that influences the onset or aggravation of a disease state through the cell surface receptor. Examples of such genes include genes that encode tumor necrosis factor receptors (TNFRs), platelet derived growth factor receptors (PDGFRs), interleukin receptors, and the like.

The target gene (b) denotes a target gene that has a mutated site and encodes a factor that induces the onset/aggravation of a disease state such as inflammation or cell death because its transcription product causes the function of a normal cell to be lost or builds up as a cytotoxic substance. Examples of such genes include Jak2 V617F mutation, ATN1 CAG repeat mutation, TTR V30M mutation, KT14 R125C mutation, and the like.

In the present invention, the target gene is preferably a gene that is expressed in a Dectin-1 expressing cell and that influences the in vivo function for which the cell is responsible. Dectin-1 is a receptor (pattern recognition receptor) that has a sugar chain recognition domain of a C-type leptin type present on the cell membrane. Dectin-1 extracellularly has a region that specifically recognizes β-1,3-glucan and intracellularly has a motif, called immunoreceptor tyrosinase-based activation motif-1 (ITAM), that delivers an activation signal. Once recognizing β-1,3-glucan, Dectin-1 facilitates production of NF-κB or an inflammatory cytokine to induce a biological defense response. In the present invention, examples of Dectin-1 expressing cells include macrophages, dendritic cells, neutrophils, and the like. It is known that schizophyllan has a β-1,3-glucan backbone, and is delivered into a Dectin-1 expressing cell through a signal induced when bound to Dectin-1 that is present on the cell membrane of a Dectin-1 expressing cell. The nucleic acid-polysaccharide complex of the present invention is delivered into a Dectin-1 expressing cell because schizophyllan, which is a component of the complex, is recognized by Dectin-1. Also, selecting an siRNA that targets a gene that influences the in vivo function for which a Dectin-1 expressing cell is responsible as the siRNA to be contained in the nucleic acid-polysaccharide complex of the present invention makes it possible to induce in vivo immunosuppression and modulate immunity.

In the case where a gene that is expressed in a Dectin-1 expressing cell and influences the in vivo function for which this cell is responsible is regarded as a target gene, the gene is not particularly limited and can be suitably selected based on the application of the complex. Examples of such genes include CD40, B7.1(CD80), B7.2(CD86), CCR7, CCL21, DC-SIGN, IL-6, IL-12, IL-15, IL-18, IFN-α, IFN-γ, and the like. Such genes also include a gene coding a protein mediating a signaling cascade. From the viewpoint of more effectively inducing immunomodulation, especially immunosuppression, in a living body, a suitable target gene may be a gene that is relevant to antigen presentation, such as a gene that encode a costimulatory factor (also called a costimulatory molecule), e.g., CD40, B7.1(CD80), and B7.2 (CD86). Inter alia, in the nucleic acid-polysaccharide complex of the present invention, use of siRNA against a gene encoding the costimulatory factor can effectively suppress rejection occurring in organ transplantation.

In a suitable example of the siRNA that constitutes the nucleic acid-polysaccharide complex of the present invention, the sense strand RNA and the antisense strand RNA are each composed of 21 ribonucleotides, with a dangling end composed of 2 ribonucleotides being formed at the 5' end of the sense strand RNA as well as the 5' end of the antisense strand RNA. That is, in the case of such a double strand RNA, the 1st to 19th ribonucleotides from the 3' end of the antisense strand RNA are complementary to the 3rd to 21st ribonucleotides from the 5' end of the sense strand RNA. Herein, such a 21 mer siRNA is also referred to as a 21 mer type siRNA. The 21 mer type siRNA is not cleavable by Dicer. Herein, the 21 mer type siRNA denotes an siRNA that exhibits an RNAi effect without being cleaved by Dicer. In the case where phosphorothioated polydeoxyadenine is added to the sense strand in the 21 mer type siRNA, the nucleic acid-polysaccharide complex of the present invention can effectively exhibit an RNA interference effect by allowing the antisense strand to be incorporate into a RISC complex.

In the present invention, an siRNA in which the number of the single strand dA bound to the double strand RNA is 1 and the single strand dA is bound to the 5' end of the sense strand is suitable. Thus, in the case where the single strand dA is bound only to the 5' end of the sense strand, the RNA interference effect based on the double strand RNA can be markedly exhibited.

Also, in the case of the 21 mer type siRNA, single strand polydeoxyadenine may be bound to any of the sense strand/antisense strand and 5' end/3' end, and in the case where single strand polydeoxyadenine is bound to, in particular, the 5' end of the sense strand, a superior RNA interference effect can be demonstrated.

The number of deoxyadenines constituting the single strand polydeoxyadenine is not particularly limited as long as a complex with schizophyllan, which will be described below, can be formed, and is, for example, 10 to 100, preferably 20 to 100, more preferably 20 to 80, and even more preferably 30 to 50.

In the nucleic acid-polysaccharide complex of the present invention, preferably, at least part of the phosphodiester links of the portion responsible for formation of a complex between siRNA and schizophyllan (i.e., polydeoxyadenine (dA) tail portion) is phosphorothioated (S modified). Herein, the extent of S modification of the dA (polydeoxyadenine) tail portion refers to the proportion (%) of S-modified phosphodiester links relative to the total phosphodiester links in the dA tail. Also, the S-modified phosphodiester link shows a binding structure in which one oxygen atom of the phosphate residue of the phosphodiester link portion is replaced by a sulfur atom.

S modification on polydeoxyadenine can be performed according to a known method. The distribution of S modification in the dA tail portion is not particularly limited, and the desired S modification may be performed on any location. The S-modified dA tail portion forms a favorable complex with schizophyllan, and the nucleic acid-polysaccharide complex obtained in this manner has a high level of resistance to degrading enzymes. The extent of S modification of the dA tail portion is usually 50% or greater, preferably 80%, and more preferably 100%.

The single strand polydeoxyadenine may be directly bound to the terminal ribonucleotide of the sense strand RNA and/or antisense strand RNA of the double strand RNA or may be bound via a linker (spacer).

The nucleic acid-polysaccharide complex of the present invention contains schizophyllan as a portion that is responsible for a desired function other than the RNA interference effect. Schizophyllan is a polysaccharide with a β-1,3-glucan backbone and is delivered into a cell through a signal that is induced when bound to Dectin-1, which is a receptor present on the surface of an antigen presenting cell.

Schizophyllan (sometimes abbreviated as SPG), which is a component of the nucleic acid-polysaccharide complex of the present invention, can be produced according to an ordinary method described in a document (A.C.S. 38(1), 253 (1997) or Carbohydrate Research, 89, 121-135 (1981)). Schizophyllan obtained in such a manner may be subjected to ultrasonication to give schizophyllan having a desired molecular weight.

In the case where a functional molecule is to be bound to SPG, the proportion of the functional molecule to be bound is, for example, 1 to 200, preferably 1 to 100, and particularly preferably 1 to 50 functional molecules relative to 100 side chains of SPG. The proportion of the functional molecule bound can be adjusted by controlling the amount of oxidizer added, such as sodium periodate, relative to the branched glucose residue in the aforementioned method.

The binding site where the functional molecule binds to SPG and the binding site where the linker for the functional molecule is bound are not particularly limited, but it is preferable that the 1,2-diol portion of glucose with a 1,6-glucopyranoside link branched from the β-1,3-glucan backbone of SPG is substituted for binding.

The molecular weight of schizophyllan used in the nucleic acid-polysaccharide complex of the present invention is not particularly limited, and suitably set according to, for example, the chain length of the dA tail. Specifically, the molecular weight of schizophyllan is usually, for example, 25000 to 500000 and preferably 25000 to 250000.

The nucleic acid-polysaccharide complex of the present invention can be prepared according to a known method. A specific example may be a production method that has the following steps (1) to (3): (1) the above-described polynucleotide-bound double strand RNA to which a single strand dA tail is bound directly or via a linker is prepared according to a known method, (2) separately, SPG is provided, or SPG (modified SPG) to which a functional molecule is bound directly or via a linker is prepared, and (3) a complex is then formed using the single strand dA tail bound to the DNA-binding double strand RNA and the SPG or modified SPG.

In the step (3) of the method, the mixing ratio of the polynucleotide-bound double strand RNA to the SPG or modified SPG can be suitably selected according to the chain length of the dA tail or the chain length of the SPG or modified SPG. In the nucleic acid-polysaccharide complex of the present invention, one glucose molecule of the SPG backbone corresponds to one adenine molecule of the dA tail, and one dA tail chain and two SPG chains form a triple helix conformation. That is, in the nucleic acid-polysaccharide complex of the present invention, the dA tail is incorporated into one or more locations of the double helix conformation formed by two SPG chains, thus forming a triple helix conformation. For example, with an siRNA to which a 40 mer dA tail is added and SPG with a molecular weight of 150000, two molecules of SPG with a molecular weight 150000 and 17 molecules of an siRNA to which 40 mer dA is added form a triple helix conformation. A preferable molar ratio of the dA tail-added siRNA to SPG is 20:1 to 1:5, and preferably, they are mixed at 10:1 to 1:1, and the single strand polydeoxyadenine region of the polynucleotide-bound double strand RNA and the SPG or modified SPG are complexed. Subjecting the siRNA and the SPG or modified SPG to complex forming conditions in such a molar ratio enables these materials to efficiently interact with each other, thus making it possible to enhance the production efficiency of the nucleic acid-polysaccharide complex of the present invention.

Specifically, formation of the triple helix conformation of the nucleic acid-polysaccharide complex of the present invention can be performed according to the following method. SPG adopts a triple helix conformation in a natural environment or in water. This SPG is dissolved in a polar solvent such as dimethylsulfoxide (DMSO) or an aqueous alkali solution such as an aqueous sodium hydroxide solution to be modified into single strands, then a dA tail-added siRNA is added, the solvent is replaced with water or the aqueous alkali solution is neutralized (regeneration process), and thereby a triple helical complex conformation (association structure) composed of one strand portion of polynucleotide linked with a double strand RNA and two strands of SPG is formed. It seems that such complex formation of a polynucleotide and a polysaccharide is mainly achieved through hydrogen bonding and a hydrophobic interaction.

The nucleic acid-polysaccharide complex of the present invention once introduced into a cell can inhibit expression of a target gene in the cell, and can thus be used as a pharmaceutical composition intended to inhibit expression of the target gene. The pharmaceutical composition can be prepared by suitably combining a therapeutically effective amount of the nucleic acid-polysaccharide complex of the present invention as an active ingredient with a pharmaceutically acceptable carrier. Examples of such a carrier include aqueous carriers such as purified water, sugar-containing aqueous solutions, buffers, physiological saline, and nuclease-free water; excipients; and the like.

The administration route of the nucleic acid-polysaccharide complex (or a fragment thereof) can be suitably selected from methods conventionally used based on the patient's symptom, disease state, disease, and the like, such as oral, parenteral (including intravenous, intraperitoneal, intramuscular, subcutaneous, intrarectal, and intravaginal administration), inhalation, systemic administration, local administration (including external application to the skin or buccal cavity; infusion onto a site that does not substantially result in entry into the blood flow, such as the eye, ear, and nose).

Because the nucleic acid-polysaccharide complex of the present invention is specifically taken up into a Dectin-1 expressing cell, setting a gene that influences the in vivo function for which the Dectin-1 expressing cell is responsible as the target gene of the siRNA makes it possible to use the siRNA also as an active ingredient of a function modulator of the Dectin-1 expressing cell. As stated above, the Dectin-1 expressing cell is a cell that is involved in immune functions, such as macrophages, dendritic cells, and neutrophils, and it is hoped that the functional modulator serves as a so-called immune function modulator. Moreover, the present invention also provides an immunomodulator containing the nucleic acid-polysaccharide complex of the present invention as an active ingredient. Various carriers that can be contained in these pharmaceutical agents, administration routes of the pharmaceutical agents, and the like are as described above.

In particular, in the case where the nucleic acid-polysaccharide complex of the present invention is used for immunomodulation (in particular, immunosuppression), a gene that encodes the aforementioned costimulatory factor (also referred to as a costimulatory molecule) is regarded as a target gene. A costimulatory factor together with a corresponding auxiliary stimulatory molecule (integrin ligand) constitutes a costimulatory pathway and functions to perform signal transduction for biological defense and also to strengthen the intracellular adhesion between an antigen presenting cell and a T-lymphocyte. A specific example of a costimulatory factor suitable in the present invention is CD40. CD40 is an antigen with a molecular weight of 50 kDa that is present on the cell membrane surface, and is expressed in a Dectin-1 expressing cell. It is known that CD40 has an important function on the proliferation and differentiation of B cells and dendritic cells. CD40 was identified as an antigen expressed on the human B cell surface, and is thought to belong to the TNF receptor family due to the homology of its amino acid sequence.

In applications of the nucleic acid-polysaccharide complex of the present invention, the ability to induce immunosuppression, for example, can be checked by a mixed lymphocyte reaction (MLR) test or a test in which inhibition of T cell proliferation is determined by measuring thymidine or bromodeoxyuridine (BrdU) uptake.

Suitably selecting a target gene makes it possible to use the nucleic acid-polysaccharide complex of the present invention in the treatment or prophylaxis of resistance or rejection to a transplanted organ or tissue (such as kidney, heart, lung, bone marrow, skin, and cornea); treatment or prophylaxis of autoimmune diseases, inflammatory diseases, proliferative and over-proliferative diseases, and cutaneous symptoms of immunologically mediated diseases (such as chronic rheumatoid arthritis, erythematodes, systemic erythematodes, Hashimoto's thyroiditis, multiple sclerosis, myasthenia gravis, type I diabetes, uveitis, nephrotic syndrome, psoriasis, atopic dermatitis, contact dermatitis, eczematous dermatitis, seborrheic dermatitis, lichen planus, pemphigus, bullous pemphigus, epidermolysis bullosa, hives, angioedema, angiitis, erythema, skin eosinophilia, and alopecia areata); and in the treatment of reversible obstructive airways diseases, gastroenteritis, allergies (such as inflammatory biliary disease, celiac disease, rectitis, eosinophilic gastroenteritis, mastocytosis, Crohn's disease, and ulcerative colitis), food-related allergies (such as migraine, rhinitis, and eczema), and other types of allergy. A person skilled in the art can determine, in order to induce immunosuppression, an effective and non-toxic amount of the nucleic acid-polysaccharide complex of the present invention by routine experimentation. Although the effective dose is not particularly limited, the effective dose in the case of using an siCD40/SPG complex can be usually selected from the range of, for example, about 0.001 to 10 mg per kg body weight per day.

Moreover, the present invention provides a method for introducing the above-described nucleic acid-polysaccharide complex into a target cell, including the step of bringing the nucleic acid-polysaccharide complex into contact with the target cell. The amount of the nucleic acid-polysaccharide complex of the present invention introduced into a cell and the introduction method may be the same as those with conventional siRNAs. Note that the nucleic acid-polysaccharide complex of the present invention, even when used singly, demonstrates strong ability to migrate into a cell, and it is thus possible to introduce the nucleic acid-polysaccharide complex into a cell without a conventional gene transfection reagent that has been used to introduce an siRNA into a cell, or with a conventional gene transfection reagent in a reduced amount. Note that the inhibition of expression of the target gene by the nucleic acid-polysaccharide complex of the present invention may be carried out in vivo as well as in vitro or ex vivo.

Also, the present invention provides use of the nucleic acid-polysaccharide complex to inhibit expression of a target gene in a cell, and use of the nucleic acid-polysaccharide complex for the manufacture of an inhibitor of target gene expression. Moreover, the present invention provides a method for inhibiting expression of a target gene including the step of bringing the nucleic acid-polysaccharide complex into contact with a cell containing a target gene. With regard to these uses and method, the nucleic acid-polysaccharide complex and the manner of using the complex are as described above.

2. Immune Function Modulator

Furthermore, the present invention provides an immune function modulator containing a nucleic acid-polysaccharide complex of schizophyllan and a polynucleotide in which polydeoxyadenine is added to an siRNA that is directed to a gene that affects the in vivo function for which an Dectin-1 expressing cell is responsible.

With regard to the immune function modulator, the target gene of the siRNA may be a gene that is expressed in a Dectin-1 expressing cell and influences the in vivo function for which the Dectin-1 expressing cell is responsible, preferably a gene that relates to the antigen presentation of the Dectin-1 expressing cell, more preferably a gene that encodes a costimulatory factor, and particularly preferably a gene that encodes CD40. Use of siRNAs that target these genes makes it possible to induce in vivo immunosuppression and modulate an immune function.

In the immune function modulator, at least part of the phosphodiester links of polydeoxyadenine added to the siRNA is phosphorothioated. The extent of S modification of polydeoxyadenine is as described in the section titled "1. Nucleic acid-polysaccharide complex containing schizophyllan and siRNA added to polydeoxyadenine that may be phosphorothioated, and applications thereof".

Also, in the nucleic acid-polysaccharide complex used in the immune function modulator, the structure of siRNA, the number of deoxyadenines constituting polydeoxyadenine, the manner of binding between siRNA and polydeoxyadenine, the structure of schizophyllan, and the like are as described in the section titled "1. Nucleic acid-polysaccharide complex containing schizophyllan and siRNA added to polydeoxyadenine that may be phosphorothioated, and applications thereof".

The immune function modulator is prepared as a pharmaceutical composition for immunomodulation by suitably combining the nucleic acid-polysaccharide complex with a pharmaceutically acceptable carrier. Carriers that may be contained in the immune function modulator are as described in the section titled "1. Nucleic acid-polysaccharide complex containing schizophyllan and siRNA added to polydeoxyadenine that may be phosphorothioated, and applications thereof".

The immune function modulator when administered into an animal (including a human) in need of modulation of an immune function brings the nucleic acid-polysaccharide complex into contact with a Dectin-1 expressing cell present in the animal, thus making it possible to inhibit expression of a target gene in the cell and modulate the immune function of the animal. Here, a specific example of modulation of an immune function may be immunosuppression. In the immune function modulator, the target gene is preferably, for example, CD40, B7.1 or B7.2 that is a costimulatory factor. Specific examples of animals in need of immunosuppression include animals in need of treatment or prophylaxis of resistance or rejection to a transplanted organ or tissue (such as kidney, heart, lung, bone marrow, skin, and cornea); animal in need of treatment or prophylaxis of autoimmune diseases, inflammatory diseases, proliferative or over-proliferative diseases, or cutaneous symptoms of immunologically mediated diseases (such as chronic rheumatoid arthritis, erythematodes, systemic erythematodes, Hashimoto's thyroiditis, multiple sclerosis, myasthenia gravis, type I diabetes, uveitis, nephrotic syndrome, psoriasis, atopic dermatitis, contact dermatitis, eczematous dermatitis, seborrheic dermatitis, lichen planus, pemphigus, bullous pemphigus, epidermolysis bullosa, hives, angioedema, angiitis, erythema, skin eosinophilia, and alopecia areata); and animals in need of treatment of reversible obstructive airways diseases, gastroenteritis, allergies (such as inflammatory biliary disease, celiac disease, rectitis, eosinophilic gastroenteritis, mastocytosis, Crohn's disease, or ulcerative colitis), food-related allergies (such as migraine, rhinitis, or eczema), animals in need of treatment of other types of allergy; and the like. In order to achieve such immunosuppression, it is preferable to administer the immune function modulator and an antigen that requires immunosuppression. For example, for animals in need of treatment or prophylaxis of resistance or rejection to a transplanted organ or tissue (such as kidney, heart, lung, bone marrow, skin, and cornea), administration to the donors and recipients for organ and tissue transplantation is performed before or after transplantation, or before and after transplantation. It is desirable to administer the immune function modulator together with a causative antigen for the treatment of allergy and autoimmune disease.

Among the immune function modulators, those that target a costimulatory factor can inhibit the expression of the costimulatory factor in a manner specific to antigen presenting cells such as dendritic cells, which enables to induce antigen-specific immunosuppression, so that efficient immunosuppression (particularly, suppression of rejection occurring in organ transplantation) is achieved with fewer side effects because such immune function modulators do not affect cells except antigen presenting cells that express a costimulatory factor.

The administration method, dosage, and the like of the immune function modulator are as described in the section titled "1. Nucleic acid-polysaccharide complex containing schizophyllan and siRNA added to polydeoxyadenine that may be phosphorothioated, and applications thereof".

In addition, the present invention also provides use of the nucleic acid-polysaccharide complex for the manufacture of an immune function modulator. Moreover, the present invention provides a method for modulating an immune function including the step of bringing the nucleic acid-polysaccharide complex into contact with an animal in need of modulation of an immune function. The present invention also provides use of the nucleic acid-polysaccharide complex for the manufacture of a pharmaceutical agent for suppressing rejection occurring in transplantation therapy. Furthermore, the present invention provides a method for suppressing rejection occurring in transplantation therapy including the step of administering the nucleic acid-polysaccharide complex to an animal in need of treatment or prophylaxis of resistance or rejection to a transplanted organ or tissue. With regard to this use and method, the nucleic acid-polysaccharide complex and the manner of using the complex are as described above.

EXAMPLES

The present invention shall be described in more detail below by way of examples, but the present invention is not limited thereto. Note that schizophyllan may be referred to as "SPG" in the examples. Also, the siRNA directed to luciferase may be referred to as "siLuc", and the siRNA directed to CD40 may be referred to as "siCD40".

Example 1: Formation of Nucleic Acid-Polysaccharide Complex of SPG and siRNA The nucleic acid-polysaccharide complexes used in the following examples were formed as follows. SPG with a molecular weight of about 150000 was prepared so as to have a final concentration of 15 mg/ml in a 0.25 N aqueous sodium hydroxide solution, then stirred for 1 hour, and left to stand at 4° C. for 1 day for modification. A solution of an siRNA to which S-modified poly(dA) dissolved in 330 mM first sodium phosphate had been added was added to this modified SPG solution, and the mixture was neutralized and left to stand at 4° C. for no less than 24 hours. At this time, the mixture was prepared so as to have 0.27 mol of SPG per mol of siRNA. Note that, in the S-modified poly(dA)-added siRNA, 40 phosphorothioated deoxyadenines were linked with the 5' end of the sense strand of the siRNA by phosphoester links. In the following examples, the S-modified poly(dA) may be referred to as dA40(s). The extent of S modification of all the S-modified polydeoxyadenines used in the following examples was 100%.

Example 2: Stability of Nucleic Acid-Polysaccharide Complex of S-Modified Poly(dA)-Added siRNA and SPG in Cell Culture Medium Preparation was carried out so as to satisfy the conditions shown in Table 1 by adding a sample to a phosphate buffer (PBS) or a cell culture medium (10% FBS+RPMI) (FBS: Biological Industries Cat #04-001-1A, RPMI: Wako Pure Chemical Industries, Ltd., Cat #189-02025)). The sample was incubated at 37° C. for 4 hours or 24 hours, then subjected to electrophoresis under 100 V and 60 min conditions using 12.5% polyacrylamide gel (Tris-borate-EDTA (TBE)), and stained with SYBR Gold (Lifetechnologies Japan).

In Table 1, in dA40(s)-siLuc(21 nt), 40 mer phosphorothioated polydeoxyadenine was added to the 5' end of the sense strand of 21 mer siRNA (SEQ ID NO. 1) directed to luciferase. In dA40(s)-siLuc(27 nt), 40 mer phosphorothioated polydeoxyadenine was added to the 5' end of the sense strand of 27 mer siRNA (SEQ ID NO. 3) directed to luciferase.

TABLE 1

| Lane | Sample | Incubation |
|---|---|---|
| 1 | dA40(s)-siLuc(27 nt) | No incubation |
| 2 | dA40(s)-siLuc(27 nt) | 10% FBS + RPMI: 37° C., 24 hours |
| 3 | dA40(s)-siLuc(27 nt)/SPG complex | 10% FBS + RPMI: 37° C., 24 hours |
| 4 | dA40(s)-siLuc(21 nt) | No incubation |
| 5 | dA40(s)-siLuc(21 nt) | 10% FBS + RPMI: 37° C., 24 hours |
| 6 | dA40(s)-siLuc(21 nt)/SPG complex | 10% FBS + RPMI: 37° C., 24 hours |
| 7 | dA40(s)-siLuc(21 nt)/SPG complex | 10% FBS + RPMI: 37° C., 4 hours |
| 8 | dA40 | No incubation |
| 9 | 10% FBS + RPMI | No incubation |

As a result, with regard to the siRNAs to which 40 mer phosphorothioated poly(dA) had been added, samples that were not in the form of a complex of an siRNA and SPG in a degrading enzyme-containing cell culture medium (lanes 2 and 5) and the controls of lanes 1 and 4 had vague bands, indicating degradation, and samples that were in the form of a complex of an siRNA and SPG (lanes 3, 6, and 7) showed clearly visible bands, indicating that nucleic acid-polysaccharide complexes were stable. Note that samples with siRNAs to which phosphorothioated poly(dA) had been added were more stable in a degrading enzyme-containing cell culture medium than those with siRNAs to which non-phosphorothioated poly(dA) had been added.

Example 3: Dicer Sensitivity of Nucleic Acid-Polysaccharide Complex (3-1) Dicer Sensitivity of Nucleic Acid-Polysaccharide Complex with Non-S-Modified dA Tail In this example, a recombinant human dicer enzyme kit (manufactured by Genlantis Inc.: Cat # T510002) was used. Also, premixes having the following components (A to E) were prepared.

A. Nucleic acid sample: 2.5 μl (25 ng)
B. 10 mM ATP: 1 μl
C. 50 mM $MgCl_2$: 0.5 μl
D. Dicer reaction buffer: 4 μl
E. Recombinant Dicer enzyme (1 unit): 2 μl Samples B to D or B to E were mixed in a PCR tube, and then nucleic acid sample A was added. Then, nuclease-free distilled water was added such that the final volume was 10 μl. Then, incubation was carried out at 37° C. for 15 hours. After incubation, a stop solution was added to stop the reaction. Electrophoresis was carried out at 150 V for 80 min using 15% polyacrylamide gel (Tris-borate-EDTA (TBE)), and the gel was stained with SYBR (r) Gold (Lifetechnologies Japan).

In Table 2, siCD40(21 nt) denotes a 21 mer siRNA (SEQ ID NOs. 5 and 6) directed to CD40. In dA40-siCD40(21 nt), 40 mer polydeoxyadenine was added to the 5' end of the sense strand (SEQ ID NO. 5) of a 21 mer siRNA (SEQ ID NOs. 5 and 6) directed to CD40. siLuc21 denotes a 21 mer siRNA directed to luciferase shown in SEQ ID NOs 1 and 2. In dA40-siLuc(21 nt), 40 mer polydeoxyadenine was added to the 5' end of the sense strand (SEQ ID NO. 1) of a 21 mer siRNA (SEQ ID NOs. 1 and 2) directed to luciferase.

TABLE 2

| Lane | Sample |
|---|---|
| 1 | Marker |
| 2 | siCD40(21 nt) |
| 3 | dA40-siCD40(21 nt) |

TABLE 2-continued

| Lane | Sample |
|---|---|
| 4 | dA40-siCD40(21 nt): Dicer added |
| 5 | siLuc(21 nt) |
| 6 | dA40-siLuc(21 nt) |
| 7 | dA40-siLuc(21 nt): Dicer added |
| 8 | siLuc(27 nt) |
| 9 | dA40-siLuc(27 nt) |
| 10 | dA40-siLuc(27 nt): Dicer added |

Results of the above-described electrophoresis show that the electrophoresis band of lane 2 was as clearly visible as that of lane 3, and the band of lane 6 was as clearly visible as that of lane 7, and thus poly(dA)-siRNA(21 nt) is not cleavable by Dicer, but on the other hand, the band of lane 10 was more vague than that of lane 9, and poly(dA)-siRNA (27 nt) is cleavable by Dicer.

(3-2) Dicer Sensitivity of Nucleic Acid-Polysaccharide Complex with S-Modified dA Tail In the same manner as in (3-1) above, the Dicer sensitivity of a nucleic acid-polysaccharide complex with an S-modified dA tail was evaluated.

TABLE 3

| Lane | Sample |
|---|---|
| 1 | Marker |
| 2 | siLuc(21 nt) |
| 3 | siLuc(27 nt) |
| 4 | dA40(s)-siCD40(21 nt) |
| 5 | dA40(s)-siCD40(21 nt): Incubation with 37° C. warm water |
| 6 | dA40(s)-siCD40(21 nt): Dicer added |
| 7 | Marker |
| 8 | siLuc(21 nt) |
| 9 | siLuc(27 nt) |
| 10 | dA40(s)-siCD40(27 nt) |
| 11 | dA40-siCD40(27 nt): Incubation with 37° C. warm water |
| 12 | dA40-siCD40(27 nt): Dicer added |

In Table 3, siLuc(21 nt) denotes a 21 mer siRNA (SEQ ID NOs. 1 and 2) directed to luciferase. siLuc(27 nt) denotes a 27 mer siRNA (SEQ ID NOs. 3 and 4) directed to luciferase. In dA40(s)-siCD40(21 nt), 40 mer phosphorothioated polydeoxyadenine was added to the 5' end of the sense strand (SEQ ID NO. 5) of a 21 mer siRNA (SEQ ID NOs. 5 and 6) directed to CD40. In dA40(s)-siCD40(27 nt), 40 mer phosphorothioated polydeoxyadenine was added to the 5' end of the sense strand (SEQ ID NO. 7) of a 27 mer siRNA (SEQ ID NOs. 7 and 8) directed to CD40.

Results of electrophoresis showed that the band of lane 6 was as clearly visible as those of lanes 4 and 5 and thus the 21 nt type siRNA, even when S-modified poly dA has been added thereto, is not cleavable by Dicer, but on the other hand, the band of lane 12 was vaguer than those of control lanes 10 and 11, and thus the 27 nt type siRNA is cleavable by Dicer.

Example 4: RNA Interference Effect of Poly(dA)-Linked siRNA

A Dual Luciferase expression vector psiCHECK™-2 (Promega Cat # C8021) was introduced into HEK 293 cells using Lipofectamine™ LTX (Lifetechnologies Japan, Cat #15338-500). At this time, the number of cells was adjusted so as to be 50000 per well. dA40-siLuc(21 nt) or dA40-siLuc(27 nt) was introduced into the cells using TransIT™-TKO (Takara Bio, Inc., Cat # V2154), and the cells were incubated at 37° C. for 20 hours in a $CO_2$ incubator. Then, a Dual Luciferase assay (manufactured by Promega, Dual-Glo Luciferase assay system, Cat# E2920) was carried out to measure the RNA interference effect. As a control, the same procedure was carried out without using a nucleic acid sample. With regard to the RNA interference effect, two luciferase expressions in the control were compared, and the RNA interference effect at that time was regarded as 0%, and the expression inhibition in each sample was expressed in %.

Results are shown in FIG. 1. It was shown that 21 mer dA40-siLuc(21 nt) linked with poly(dA), even without being cleaved by Dicer, yields the same RNA interference effect activity as 27 mer dA40-siLuc(27 nt).

Example 5: RNA Interference Effect of siRNA/SPG Complex Linked with S-Modified Poly(dA)

The RNA interference effect of a complex of SPG and a chimeric siRNA with phosphorothioated poly(dA) was evaluated using a Dual Luciferase assay (manufactured by Promega, Dual-Glo Luciferase assay system, Cat # E2920). RAW264.7 cells (dRAW cells), which strongly express Dectin-1, were used (obtained from associate professor Yoshiyuki Adachi (immunology) at Department of Pharmacology, Tokyo University of Pharmacy and Life Sciences). Samples used are shown in Table 4 below. In sample 4 in Table 3, dA40(s)-siLuc(21 nt) was introduced using a TransIT™-TKO (Takara Bio, Inc., Cat # V2154).

Results are also shown in Table 4 below.

TABLE 4

| Sample | TransIT-TKO concentration (µl/ml) | siRNA concentration (nM) | RNA interference effect (%) |
|---|---|---|---|
| 1 Control (psiCHECK ™-2 Co-Transfection) | — | 10 | 0 |
| 2 siLuc(21 nt) | — | 10 | 8.8 |
| 3 dA40(s)-siLuc(21 nt) | — | 10 | −4 |
| 4 dA40(s)-siLuc(21 nt) (TransIT-TKO added) | 0.1 | 10 | 1.8 |
| 5 dA40(s)-siLuc(21 nt)/SPG complex | — | 10 | 41 |

According to Table 4, it was shown that the poly(dA)(s)-siRNA/SPG complex yields an RNA interference effect.

Example 6: Dose Dependency of RNA Interference Effect by Poly(dA)(s)-siRNA Complex In this example, the dose dependency of siRNA activity was checked. dRAW cells, which are proliferative in a 10% seroculture, were used. Samples used in this example are shown in Table 5 below.

This example was carried out according to the following procedure.

dRAW cells were recovered, seeded onto a 48-well plate so as to be 20000 cells/well/200 µl, incubated in a $CO_2$ incubator at 37° C. for 20 hours. A psiCHECK™-2/LTX complex in an amount of 20 µl/well and a culture medium in an amount of 180 µl/well were added to the 48-well plate. Then, a Dual Luc assay (manufactured by Promega, Dual-Glo Luciferase assay system, Cat #: E2920) was carried out. Results are shown in Table 5 below.

TABLE 5

| | Sample | siRNA concentration (nM) | RNA interference effect (%) |
|---|---|---|---|
| 1 | Control (Co-transfection) | 0 | 0 |
| 2 | Naked dA40(s)-siLuc(21 nt) | 100 | 14 |
| 3 | dA40(s)-siLuc(21 nt)/SPG complex | 1 | 12 |
| 4 | dA40(s)-siLuc(21 nt)/SPG complex | 10 | 21 |
| 5 | dA40(s)-siLuc(21 nt)/SPG complex | 100 | 36 |

From Table 5, it was shown that the poly(dA)(s)-siRNA complex yields an RNA interference effect in a dose dependent manner.

Example 7: Cell Introducibility of Poly(dA)(s)-siRNA Complex (7-A) Introducibility into dRAW Cells dRAW cells were seeded so as to be 1000000 cells/dish (5 ml) and incubated in a $CO_2$ incubator at 37° C. for 20 hours. Then, Alexa 647-labeled naked dA40(s)-siLuc(21 nt) and an Alexa 647-labeled dA40(s)-siLuc(21 nt)/SPG complex were added to culture media each in a concentration of 100 nM and brought into contact with dRAW cells. After each siRNA was added, cells were recovered 1, 2, 4, and 8 hours later. The recovered cells were fixed by 10% equilibrated formaldehyde (100 μl/dish), and the number of cells labeled with Alexia 647 was measured by flow cytometry (FACS).

According to the results, the number of cells labeled with Alexia 647 using the dA40(s)-siLuc(21 nt)/SPG was more than two times greater the number of labeled cells obtained using naked dA40(s)-siLuc(21 nt), and it seems that the cellular uptake of the dA40(s)-siLuc(21 nt)/SPG complex is more than two times greater.

(7-B) Introducibility into CD11c(+)

Spleen cells were obtained from mice (C57BL/6, male, 7 weeks old; 4 mice) in accordance with a standard method. Some of the obtained spleen cells were stored under refrigeration for use as a control. The remaining spleen cells were separated into a CD11c(−) cell group and a CD11c(+) cell group using a MACS MS column. Cell separation by the column was carried out twice. The CD11c(+) cell group was prepared so as to have $7 \times 10^5$ cells, and cultured on a 6-well plate (2 ml volume) for 48 hours (37° C., 5% $CO_2$) so as to satisfy the conditions shown in Table 6 below. After culturing, FACS analyses were carried out using the FACS antibodies shown in the parentheses in Table 6. In the table, Dectin-1-FITC denotes an anti-Dectin-1 antibody modified with FITC, CD11c-FITC denotes an anti-CD40 antibody modified with FITC, and PE Isotype control denotes an isotype control antibody modified with PE.

TABLE 6

| | Sample |
|---|---|
| 1 | CD11c(−) cells (Dectin-1-FITC) |
| 2 | CD11c(+) cells (PE Isotype control) |
| 3 | CD11c(+) cells (CD11c-FITC) |
| 4 | CD11c(+) cells (Dectin-1-FITC) |
| 5 | CD11c(+) cells + SPG (Dectin-1-FITC) |
| 6 | CD11c(+) cells + 100 nM naked dA40(s)-siCD40(27 nt) (Dectin-1-FITC) |
| 7 | CD11c(+) cells + 100 nM dA40(s)-siCD40(27 nt)/SPG complex (Dectin-1-FITC) |

It was confirmed from the results that sample 5 has a smaller proportion of Dectin-1 positive cells than sample 4, sample 7 has a smaller proportion of Dectin-1 positive cells than samples 4 and 6, and when the siRNA/SPG complex is taken up into Dectin-1 expressing cells, the Dectin-1 expression level of the cells is decreased.

(7-C) Incorporation into RLC (RISC Loading Complex)

Spleen cells were obtained from mice (C57BL/6, male, 7 weeks old; 4 mice) in accordance with a standard method. Some of the obtained spleen cells were stored under refrigeration for use as a control. The remaining spleen cells were separated into a CD11c(−) cell group and a CD11c(+) cell group using a MACS MS column. Cell separation by the column was carried out twice. A CD11c(+) cell group was prepared so as to have $2 \times 10^4$ cells and cultured on a chamber cover glass (4 wells, 1 ml/well volume) for 24 hours (37° C., 5% $CO_2$). Then, siLuc in which the 5' end of the antisense strand had been labeled with Alexa 647 and a dA40(s)-siLuc/SPG complex in which the 5' end of the antisense strand had been labeled with Alexa 647 were added to CD11c(+) cells so as to achieve 100 nM, and the cells were cultured for 1 hour (37° C., 5% $CO_2$).

One hour later, the culture supernatant was removed by suction. 500 ml of a 4% paraformaldehyde/PBS solution was added to each well, and the cells were incubated for 15 minutes at room temperature. After removing the paraformaldehyde/PBS solution by suction, 1 ml of PBS was added to each well, the cells were incubated at room temperature for 5 minutes, and then PBS was removed by suction. This procedure was repeated once again (below, the procedure for 5 minute incubation at room temperature with PBS will be referred to as a washing procedure). 500 ml of a 0.1% Triton X-100/PBS solution was added to each well, the cells were incubated at room temperature for 10 minutes, and then the 0.1% Triton X-100/PBS solution was removed by suction. The washing procedure was carried out twice. 500 ml of a 10% normal goat serum (NGS)/PBS solution was added to each well, and the cells were incubated at room temperature for 30 minutes. After removing the 10% NGS/PBS solution by suction, an anti-TRBP2 mouse antibody was prepared so as to achieve 130 ng/ml with 0.1% Triton X-100, 1.5% NGS, and BSA/PBS, then 500 ml of the antibody was added to each well, and the cells were incubated at room temperature for 2 hours. The antibody solution was removed by suction, and the washing procedure was carried out 3 times. An Alexa 488 anti-mouse IgG antibody (Lifetechnologies Japan) was diluted 750-fold with Triton X-100, 1.5% NGS, and BSA/PBS, and the cells were incubated at room temperature for 1 hour. The antibody solution was removed by suction, and the washing procedure was carried out 3 times. After removing PBS by suction, the chamber was taken away, and a sample was mounted using a mounting medium containing an anti-fading agent. An image of this sample was taken with a laser confocal microscope and analyzed.

It was confirmed from the results that the siRNA of the dA40(s)-siLuc/SPG complex that had been taken up into the cells and TRBP2, which is the core protein of RLC, were localized in the same location, and images matched in the same focal depth. It is clear from the results that the siRNA taken up into the cells and TRBP2 are located within such a distance that they can interact with each other, or that is, the siRNA is incorporated in RLC. On the other hand, in the case where Alexa 647-labeled siLuc was used singly, no incorporated siLuc was observed.

(7-D) Inhibition of CD40 mRNA Expression In Vitro
(i) Real Time PCR

Passage-cultured dRAW cells (80% confluency) were suspended in a culture medium (10% FBS-RPMI (Lifetechnologies Japan, cat No. 12718011S)) and prepared so as to have $1 \times 10^5$ cells/ml. The cell suspension was added to a 96-well plate so as to have 10000 cells per well (100 µl/well) and cultured overnight under 37° C. and 5% $CO_2$ conditions. After culturing, the culture supernatant was removed by an aspirator, and 100 µl of a culture medium was added to each well. This procedure was repeated twice. The samples (Table 7) each adjusted so as to have a concentration of 100 nM using a culture medium in advance were added in an amount of 100 µl per well, and cultured for 20 hours under 37° C. and 5% $CO_2$ conditions. After culturing, 100 µl of a culture medium was added to each well, and the culture medium was then removed by an aspirator. 60 ng/ml of interferon-gamma (IFN-γ, PeproTech, cat No. 315-05) prepared using a culture medium in advance was added in an amount of 100 µl per well, and cultured for 4 hours under 37° C. and 5% $CO_2$ conditions. After culturing, total RNAs were prepared using a CellAmp Direct RNA Prep kit (Takara Bio, Inc., cat No. 37329) from the cells of each well. With the prepared total RNAs as templates, cDNAs were synthesized using a Primer Script RT reagent kit (Takara Bio, Inc., cat No. RR037A). The synthesized cDNAs were subjected to real time qPCR using SYBR Prime Ex Taq II (Takara Bio, Inc., cat No. RR081A) to measure CD40 mRNA expression levels. At the same time, the beta-actin mRNA expression levels were measured, and this was used to correct the measured CD40 mRNA values. The corrected values were regarded as the CD40 mRNA expression levels in respective conditions. The primer sequences used for qPCR are as shown in Table 8.

TABLE 7

| | Sample |
|---|---|
| 1 | No sample |
| 2 | dA40(s)-siCD40(21 nt)/SPG complex |
| 3 | SPG only |
| 4 | Naked dA40(s)-siCD40(21 nt) |

TABLE 8

| Mouse CD40 primer | Forward primer | CAAGGATTGCGAGGCATGTG | SEQ ID NO. 9 |
|---|---|---|---|
| | Reverse primer | TGACAGACGGTATCAGTGGTCTCAG | SEQ ID NO. 10 |
| Mouse β-actin primer | Forward primer | TGGCACCCAGCACAATGAA | SEQ ID NO. 11 |
| | Reverse primer | CTAAGTCATAGTCCGCCTAGAAGCA | SEQ ID NO. 12 |

It was confirmed from the results that the CD40 expression level achieved by the addition of only SPG or naked siCD40 to Dectin-1 expressing cells was not lower than that achieved by the control (no sample), or no RNAi activity was induced, but the addition of a siCD40/SPG complex to Dectin-1 expressing cells inhibited CD40 mRNA expression without weakening the original RNAi activity of the siRNA.

(ii) FACS

CD11(+) cells in mouse spleen cells were separated, and the proportion of CD40 positive cells in the CD11(+) cells was analyzed by FACS. Moreover, the same environment as in cell culturing was used, or that is, cells were added to a 10% FBS+RPMI culture medium and cultured for specified 4 hours to 48 hours after being warmed to 37° C. in $CO_2$ incubation. At this time, the CD11(+) cells were treated with SPG, naked dA40(s)-siCD40(27 nt), and a dA40(s)-siCD40 (27 nt)/SPG complex, and the subsequent CD40 expression was analyzed by FACS. The method for treating the spleen cells is as described in (7-B) above. The antibodies used in FACS are shown in the parentheses in Table 9 below. In the table, PE Isotype control denotes an isotype control antibody modified with PE, and CD40-PE denotes an anti-CD40 antibody modified with PE.

TABLE 9

| | Sample |
|---|---|
| 1 | CD11c(+) cells (PE isotype control) |
| 2 | CD11c(+) cells (CD40-PE) |
| 3 | CD11c(+) cells + 100 nM naked dA40(s)-siCD40(27 nt) (CD40-PE) |
| 4 | CD11c(+) cells + 100 nM dA40(s)-siCD40(27 nt)/SPG complex (CD40-PE) |

Results showed that expressed CD positive cells are decreased with sample 4 and the siCD40/SPG complex inhibits CD40 expression on the primary cell surface. On the other hand, with siCD40 not in the form of a complex with SPG, no reduction in the number of CD40 positive cells was observed, and it was not possible to sufficiently inhibit CD40 expression.

It seems that in this example, a complex of an siRNA and SPG was formed, and thus the siRNA was stabilized in the serum and blood, thereby enabling the siRNA to be more efficiently introduced into cells than the naked siRNA and to be delivered into the cytoplasm, and as a result, mRNA expression was inhibited, and target molecule expression on the cellular membrane surface was inhibited.

Example 8

A costimulatory factor CD40, which is a known early response factor of an immunoreaction, was set as a target molecule, and cells of a responder mouse were treated with an siRNA directed to this molecule. The pharmacological effect was evaluated by carrying out a mixed lymphocyte reaction (MLR) between a stimulator cell group and an siRNA-treated or -untreated responder cell group and measuring the cell proliferation rates of the respective groups by a BrdU chemoluminescence kit.

Figure 2:
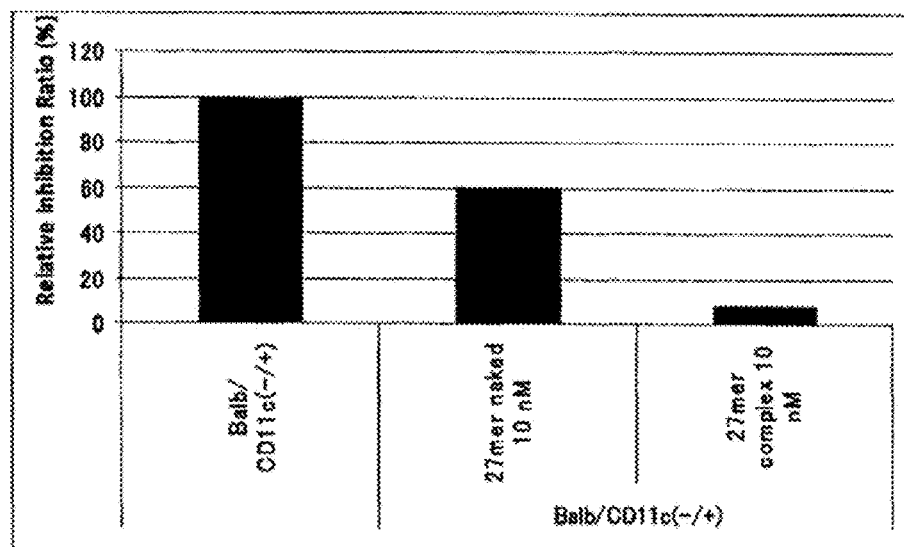
FIG. 2 is a chart showing the results of Example 8, i.e., inhibition of proliferation recovery by an alloreaction.
Figure 3:
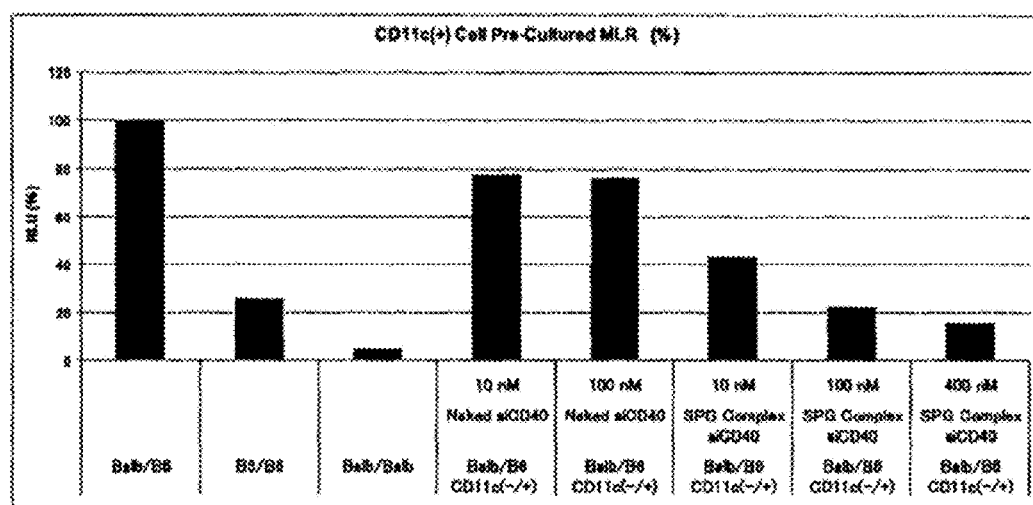
FIG. 3 is a chart showing the results of Example 8, or that is, CD11c positive cells with a dA40(s)-siCD40(27 nt)/SPG complex induce immunosuppression in preculture MLR.

When carrying out MLR, use of CD11c(−) responder spleen cells makes antigen presenting cells (APCs) deficient, thus suppressing a normal lymphocyte reaction and inhibiting cell proliferation. CD11c(+) spleen cells treated with an siCD40/SPG complex was added thereto, and the extent of cell proliferation recovery was observed. It was confirmed, from a comparison of allogeneic MLR and syngeneic MLR to which a dA40(s)-siCD40(27 nt)/SPG complex was added or not added, that notable induction of immunosuppression was achieved by adding the dA40(s)-siCD40(27 nt)/SPG complex (the extent of cell proliferation recovery was reduced: FIGS. 2 and 3).

In this example, a C57BL/6 mouse was used as a responder mouse, and Balb/c was used as a stimulator mouse. During MLR, the stimulator spleen cells were used after the cell proliferation of the stimulator spleen cells were stopped by mitomycin C (MMC) added when harvesting the stimulator spleen cells.

Pre-culture in vitro MLR refers to a method in which an siCD40/SPG complex is added to CD11c positive cells separated from the responder mouse spleen cells, then cells were brought back to a CD11 negative cell group and then mixed with mitomycin C (MMC)-treated stimulator spleen cells, and an MLR reaction is observed. That is, a dA40(s)-siRNA/SPG complex was bound (or introduced) to the target cells in advance, and immunosuppression induction in the MLR reaction was evaluated.

(8-A): Immunosuppressing Effect by Nucleic Acid-Polysaccharide Complex in Pre-Culture MLR Using CD11c Positive Cells In this test, whether the dA40(s)-siCD40(27 nt)/SPG complex demonstrates an immunosuppressing action or not was checked.

Cell Preparation

Spleen cells were collected from mice (Balb/c (9 weeks old male, 2 mice) and C57BL/6 (9 weeks old male, 2 mice)). Hemolyzing agents (ammonium chloride, potassium) were added to dissolve erythrocytes (5 ml hemolyzing agent, 5 ml RPMI). Cells were suspended in 10% FBS (DS Pharma Biomedical Co., Ltd.)+RPMI (5 ml), and the responder spleen cells were treated with mitomycin C (MMC) (25 μg MMC added to final $10^7$ cells).

Purification of CD11c Positive Cells (Magnetic Labeling)

Cells collected from the spleen cells were adjusted so as to have $10^8$ cells/sample and suspended in a buffer solution (400 μl). 100 μl of CD11c microbeads were added, and the cells were left to stand still in a refrigerator (2 to 8° C.) for 15 minutes.

Magnetic Separation

A column was rinsed with a buffer solution (MACS buffer: 2 mM EDTA, 0.5% BSA in PBS (1×) degassed after preparation), 500 μl of a suspension of magnetically labeled cells was poured with a pipette and allowed to flow out. The fluid that had flowed out was collected and used as CD11c (−) cells.

Procedure of Complex Group Addition

The collected CD11c positive cells were divided so as to be $1.0 \times 10^5$ cells/condition. Naked siCD40 and an siCD40/SPG complex were added thereto so as to have a final concentration of 100 nM, and the cells were incubated at 37° C. for 4 hours. $5 \times 10^5$ of responder cells (splenocytes) and $5 \times 10^8$ of stimulator cells (a mixture of $2.5 \times 10^4$ of CD11c positive cells and $4.75 \times 10^5$ of CD11c negative cells) were used in MLR. MLR conditions are shown in Table 10 below.

TABLE 10

MLR conditions

| Sample | |
|---|---|
| 1 | Allogeneic MLR Balbc/C57BL6 CD11c (−/+) control |
| 2 | Allogeneic MLR Balbc/C57BL6 CD11c (−/+) naked dA40(s)-siCD40 10 nM |
| 3 | Allogeneic MLR Balbc/C57BL6 CD11c (−/+) dA40(s)-siCD40/SPG complex 10 nM |

C57BL6 CD11c (−/+): The ratio of CD11c(−) cells and CD11c(+) cells mixed was CD11c(−):CD11c(+) = 95:5.
In the table, unless specified otherwise, stimulator spleen cells were MMC-treated.
In the table, MLR cells indicated as (Balbc/C57BL6) denote (mouse strain of lymphocytes used as stimulator/mouse strain of lymphocytes used as responder).
In the table, siCD40 has base sequences shown in SEQ ID NOs. 7 and 8.

Results are shown in FIG. 2. FIG. 2 shows inhibition of proliferation recovery by an alloreaction. No cell proliferation was observed when all Balb/c spleen cells and CD11c (−) cells separated from C57BL/6 were subjected to MLR. On the other hand, when all Balb/c spleen cells and CD11c (−/+) cells separated from C57BL/6 were subjected to MLR, an allogeneic reaction was activated and a cell proliferation reaction was recovered. In the case where a complex was brought into contact with the target CD11c(+) cells, and then the cells were mixed back with CD11c(−) cells and subjected to MLR together with Balb spleen cells, cell proliferation recovery was inhibited. That is, it was shown that CD11c positive cells induce immunosuppression in pre-culture MLR.

(8-B): Dose Dependency of Immunosuppressive Action by Nucleic Acid-Polysaccharide Complex Using CD11c Positive Cells In this experiment, whether or not the dA40(s)-siCD40(27 nt)/SPG complex demonstrates an immunosuppressive action in a dose dependent manner was checked. Preparation of cells was carried out in the same manner as in (A) above using mice (Balb/c (7 week old males, 2 mice), C57BL/6 (7 week old males, 2 mice)). Also, purification and magnetic separation of CD11c positive cells were carried out in the same manner as in (A) above. MLR conditions are shown in Table 11 below.

TABLE 11

MLR conditions

| Sample | |
|---|---|
| 1 | Allogeneic MLR (Balbc/C57BL6) |
| 2 | Syngeneic MLR (C57BL6/C57BL6) |
| 3 | Syngeneic MLR (Balbc/Balbc) |
| 4 | Allogeneic MLR (Balbc/C57BL6) CD11c (−/+) naked dA40(s)-siCD40(21 nt) 10 nM |
| 5 | Allogeneic MLR (Balbc/C57BL6) CD11c (−/+) naked dA40(s)-siCD40(21 nt) 100 nM |
| 6 | Allogeneic MLR (Balbc/C57BL6) CD11c (−/+) dA40(s)-/siCD40(21 nt) SPG complex 10 nM |
| 7 | Allogeneic MLR (Balbc/C57BL6) CD11c (−/+) dA40(s)-siCD40(21 nt)/SPG complex 100 nM |
| 8 | Allogeneic MLR (Balbc/C57BL6) CD11c (−/+) dA40(s)-siCD40(21 nt)/SPG complex 400 nM |

In the table, unless specified otherwise, stimulator cells were MMC-treated.
In the table, MLR cells are indicated as (mouse strain of lymphocytes used as stimulator/mouse strain of lymphocytes used as responder).

Results of MLR are shown in FIG. 3. FIG. 3 shows that CD11c positive cells induce immunosuppression in a dose dependent manner in pre-culture MLR.

Example 9

(9-A) In Vitro MLR

In this experiment, the lymphocyte growth inhibitory effect of the dA40(s)-siCD40(21 nt)/SPG complex administered in vitro was evaluated. The cell preparation method is as follows.

Spleen cells were collected from mice (stimulators: Balb/c (7 weeks old male, 2 mice) and responders: C57BL/6 (7 weeks old male, 2 mice)). Hemolyzing agents (ammonium chloride, potassium) were added to dissolve erythrocytes (3 ml hemolyzing agent, 2 min). 8 ml of RPMI was added, and the mixture was centrifuged at 300×g for 10 minutes. The supernatant was removed by an aspirator, and 10 ml of RPMI was added thereto to suspend the cells. Centrifugation and subsequent procedures were repeated. The supernatant was removed by an aspirator, then cells were suspended in 5 ml of 10% FBS/RPMI, and the cell count was measured. The spleen cells of the stimulator was treated with mitomycin C (MMC) (37° C., 30 min) (25 µg of MMC was added to the final $10^7$ cells). After MMC treatment, cells were suspended in 10 ml of RPMI and centrifuged at 300×g for 10 minutes. The supernatant was removed by an aspirator, 10 ml of RPMI was added thereto, and centrifugation and subsequent procedures were repeated 4 times. The supernatant was removed by an aspirator, then cells were suspended in 3 ml of 10% FBS/RPMI, the cell count was measured, and the cell concentration was adjusted so as to be $5\times10^6$ cells/ml. The complex (or siMOCK) was added to the spleen cells ($5\times10^6$ cells for each condition) of the responder so as to have a final concentration of 10 nM, and the cells were cultured for 4 hours at 37° C. After culturing, 10 ml of RPMI was added to the cell fluid to suspend the cells, and the cells were centrifuged at 300×g for 10 minutes. The supernatant was removed by an aspirator, 10 ml of RPMI was added thereto, and centrifugation and subsequent procedures were repeated 2 times. Cells were suspended in 1 ml of 10% FBS/RPMI, the cell count was measured, and the cell concentration was adjusted so as to be $5\times10^6$ cells/ml. $5\times10^5$ of the stimulator cells and $5\times10^5$ of the responder cells were mixed in one well (a final volume of 200 ml/well), and the cells were cultured in a 37° C. and 5% $CO_2$ environment for 72 hours. After culturing, cell growth was measured by an assay that uses chemoluminescence by BrdU uptake (Cell Proliferation ELISA, BrdU) (Roche Applied Science).

Also, in vitro MLR was carried out in which stimulator spleen cells were treated with an siRNA. The above-described procedure was carried out except that siRNA treatment was carried out after MMC treatment of stimulator cells and that responder cells after cell counting were stored under refrigeration without being treated until the beginning of MLR. MLR conditions are shown in Table 12.

TABLE 12

| | Sample |
|---|---|
| | MLR conditions (case where sample is added to responder spleen cells) |
| 1 | Syngeneic MLR (C57BL6/C57BL6) |
| 2 | Allogeneic MLR (Balbc/C57BL6) |
| 3 | Allogeneic MLR (Balbc/C57BL6) dA40(s)-siCD40/SPG complex 10 nM |
| 4 | Allogeneic MLR (Balbc/C57BL6) siMOCK (PBS) |
| | MLR conditions (case where sample is added to stimulator spleen cells) |
| 1 | Syngeneic MLR (C57BL6/C57BL6) |
| 2 | Allogeneic MLR (Balbc/C57BL6) |
| 3 | Allogeneic MLR (Balbc/C57BL6) dA40(s)-siCD40/SPG complex 10 nM |
| 4 | Allogeneic MLR (Balbc/C57BL6) siMOCK (PBS) |
| 5 | Allogeneic MLR (Balbc/C57BL6) SPG only (equivalent to 10 nM siRNA of complex) |
| 6 | Allogeneic MLR (Balbc/C57BL6) naked dA40(s)-siCD40 10 nM |

It was confirmed from the results that in the MLR of responder cells treated with the dA40(s)-siCD40/SPG complex, the cell growth was about 60% of the cell growth with control siMock, and in the MLR of stimulator cells treated with the dA40(s)-siCD40/SPG complex, the cell growth was about 50% of the cell growth with control siMock. That is, it was confirmed that irrespective of the stimulator spleen cells or responder spleen cells, addition of the dA40(s)-siCD40/SPG complex inhibits the allogeneic MLR response to the syngeneic MLR response level. It is clear from these facts that the dA40(s)-siCD40/SPG complex significantly inhibits lymphocyte activation.

(9-B) Ex Vivo MRL

In this experiment, the behavior of siRNA in a living body was examined by administering a dA40(s)-siCD40(21 nt)/SPG complex into responder mice by a caudal vein injection (i.v.), collecting spleen cells after a lapse of 4 hours, and carrying out MLR with stimulator mouse spleen cells. The cell preparation method is as follows.

Spleen cells were collected from mice (stimulators: Balb/c (8 weeks old male, 3 mice) and responders: C57BL/6 (8 weeks old male, 3 mice)). An siRNA/SPG complex was intravenously injected into the responder mice 4 hours before collecting spleen cells. Hemolyzing agents (ammonium chloride, potassium) were added to dissolve erythrocytes (5 ml hemolyzing agent, 5 ml RPMI). Cells were suspended in 5 ml of 10% FBS (DS Pharma Biomedical Co., Ltd.)+RPMI ($4\times10^5$ cells/wel), and the stimulator spleen cells were treated with mitomycin C (MMC) (25 µg MMC added to final $10^7$ cells). MLR conditions are shown in Table 14 below.

TABLE 13

| | MLR conditions |
|---|---|
| | Sample |
| 1 | Medium |
| 2 | Allogeneic MLR Balbc (MMC)/B6 (PBS) |
| 3 | Allogeneic MLR Balbc (MMC)/B6 (20 µg SPG i.v.) |
| 4 | Allogeneic MLR Balbc (MMC)/B6 (20 µg naked dA40(s)-siCD40(21 nt) i.v.) |
| 5 | Allogeneic MLR Balbc (MMC)/B6 (20 µg dA40(s)-siCD40(21 nt)/SPG complex i.v.) |
| 6 | Syngeneic MLR B6 (PBS i.v.)/B6 (PBS i.v.) |

Figure 4:
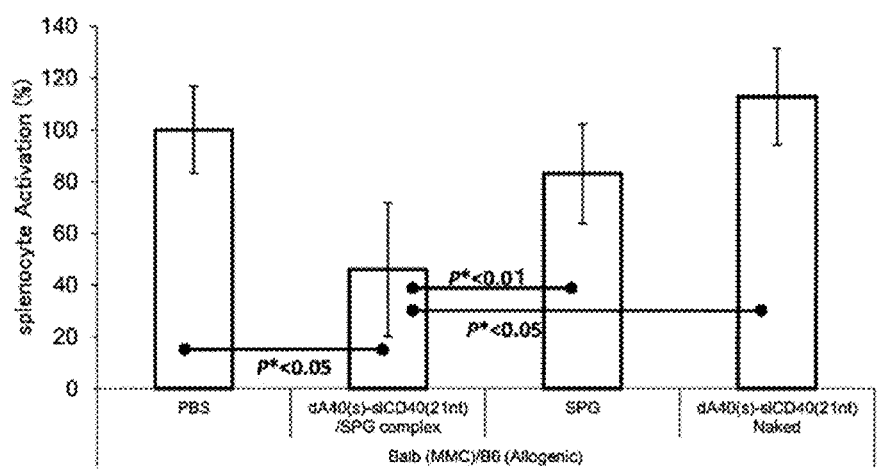
FIG. 4 is a chart showing the results of Example 9 (9-B), or that is, a dA40(s)-siCD40(21 nt)/SPG complex significantly inhibited activation of lymphocytes in ex vivo MLR.

Results are shown in FIG. 4. In FIG. 4, the value (splenocyte activity) obtained by subtracting the numerical value of the syngeneic reaction from the numerical value of the allogeneic reaction of a control (value obtained by subtracting the sample 2 cell count from the sample 6 cell count) is plotted as 100%, and how much the lymphocyte proliferative reaction resulting from the allogeneic reaction was inhibited by the administration of the dA40(s)-siCD40(21 nt)/SPG complex is shown. It is clear from the results that the dA40(s)-siCD40(21 nt)/SPG complex significantly inhibits lymphocyte activation by administration into a living body.

Example 10: Cellular Uptake Specific to Dectin-1 Expression Cells

In this experiment, specific uptake of an Alexa 647-labeled dA40(s)-siLuc(21 nt)/SPG complex into Dectin-1 expressing cells was evaluated. The test method is as follows.

A 4-well chamber was coated with collagen Type I-P. Next, 500 µl of HEK 293 T cells and dHEK cells in a concentration of $1\times10^5$ cells/ml was added, and cultured overnight (37° C., 5% $CO_2$). Then, the culture medium was replaced to add a culture medium containing a 10 nM or 100 nM Alexa 647-labeled dA40(s)-siLuc(21 nt)/SPG complex, and cells were incubated for 2 to 8 hours at 37° C. in 5% $CO_2$. Next, cells were washed twice with PBS and fixed with 10% equilibrated formaldehyde. The fixed cells were observed under a laser confocal microscope (Carl Zeiss LSM710 NLO System), and the fluorescence intensity of Alexa 647 exhibited by the cells was measured by flow cytometry. Moreover, the level of Dectin-1 expressed on the surface of the fixed cells was measured by flow cytometry using an FITC-labeled antibody.

Note that the HEK 293 T cells used in this experiment are non-Dectin-1 expressing human embryonic kidney epithelial cells, and the dHEK cells are HEK 293 T cells that have been transformed so as to express Dectin-1.

Figure 5:
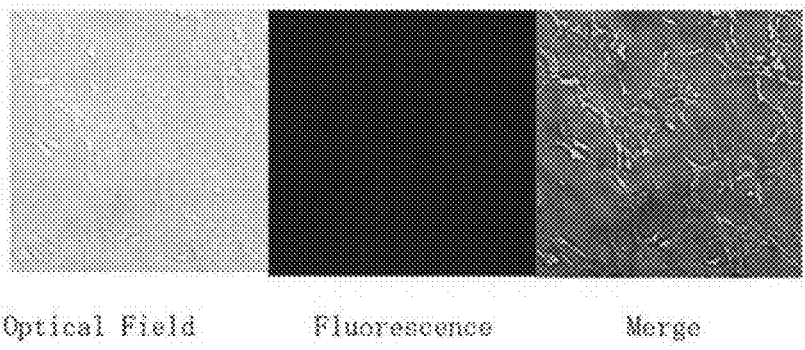
FIG. 5 shows images indicating the results of Example 10, i.e., HEK 293 T cells and dHEK cells treated with an Alexa 647-labeled dA40(s)-siLuc(21 nt)/SPG complex.
Figure 5:
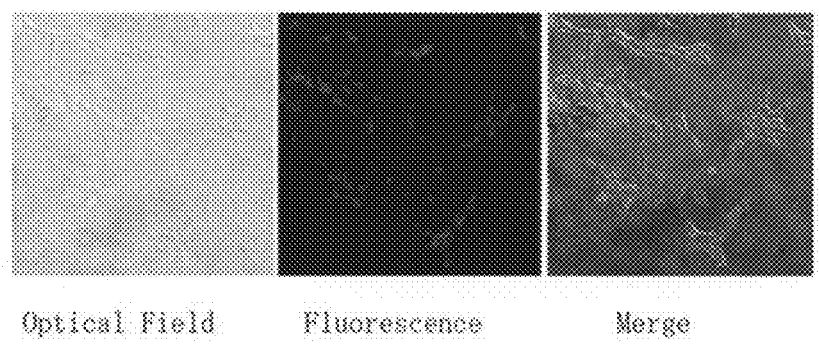
Figure 6:
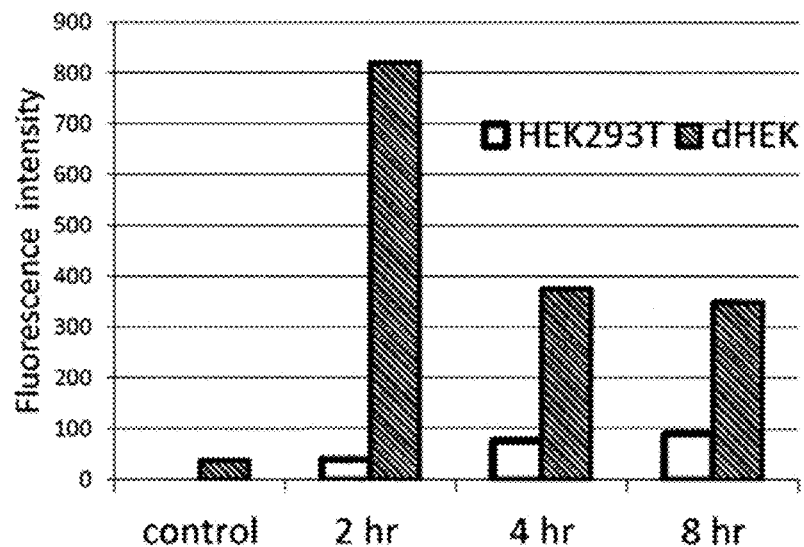
FIG. 6 shows the results of Example 10. That is, with regard to HEK 293 T cells and dHEK cells treated with an Alexa 647-labeled dA40(s)-siLuc(21 nt)/SPG complex, a chart showing the results of measuring the level of complex uptake (fluorescence intensity of Alexa 647) (FIG. 6A) and a chart showing the level of Dectin-1 expression on the cell surface (fluorescence intensity of FITC) (FIG. 6B).
Figure 6:
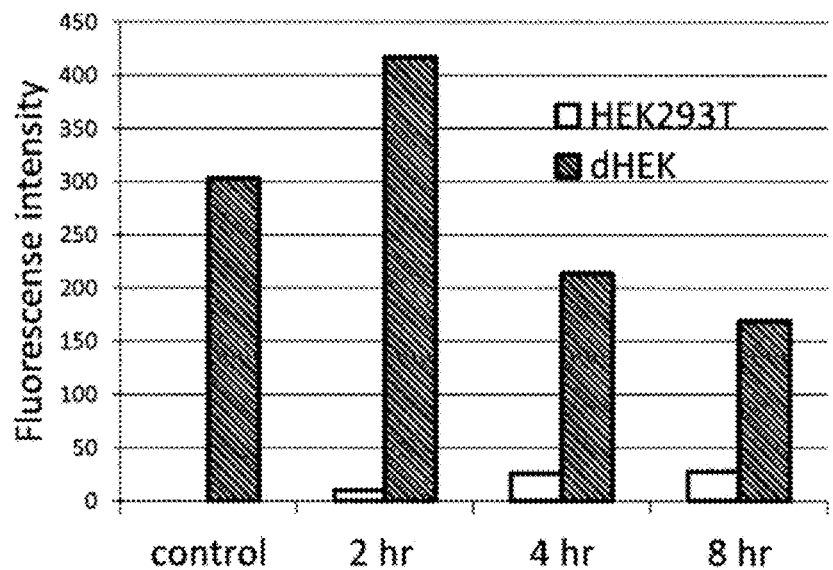

The obtained results are shown in FIGS. 5 and 6. FIG. 5 shows images of cells treated with the Alexa 647-labeled dA40(s)-siLuc(21 nt)/SPG complex, FIG. 6A shows the results of measuring the intensity of Alexa 647 fluorescence of the cells treated with the Alexa 647-labeled dA40(s)-siLuc(21 nt), and FIG. 6B shows the results of measuring the intensity of FITC fluorescence of the cells treated with the Alexa 647-labeled dA40(s)-siLuc(21 nt). It is clear from the results that the uptake of the Alexa 647-labeled dA40(s)-siLuc(21 nt)/SPG complex is confirmed only in Dectin-1-expressing dHEK cells, and the nucleic acid-polysaccharide complex of the present invention is taken up by endocytosis in Dectin-1 expression cells. Also, it is clear that the level of Dectin-1 expressed in dHEK cells decreases as the dA40(s)-siLuc(21 nt)/SPG complex is taken up, and thus Dectin-1 is taken up into the cells together with the dA40(s)-siLuc(21 nt)/SPG complex.

Example 11

11-A

In this experiment, the behavior of siRNA in a living body was examined by administering a dA40(s)-siCD40(21 nt)/SPG complex into responder mice by a caudal vein injection (i.v.), collecting spleen cells after a lapse of 4 hours, and carrying out MLR with stimulator mouse spleen cells. The cell preparation method is as follows.

Spleen cells were collected from mice (stimulators: Balb/c (8 weeks old male, 3 mice) and responders: C57BL/6 (8 weeks old male, 3 mice)). An siRNA/SPG complex was intravenously injected into the responder mice 4 hours before collecting spleen cells. Hemolyzing agents (ammonium chloride, potassium) were added to dissolve erythrocytes (5 ml hemolyzing agent, 5 ml RPMI). Cells were suspended in 5 ml of 10% FBS (DS Pharma Biomedical Co., Ltd.)+RPMI ($4 \times 10^5$ cells/wel), and the stimulator spleen cells were treated with mitomycin C (MMC) (25 μg MMC added to final $10^7$ cells). MLR conditions are shown in Table 14.

TABLE 14

| MLR conditions |
| --- |
| Sample |
| 1 Medium |
| 2 Allogeneic MLR Balbc (MMC)/B6 (PBS) |
| 3 Allogeneic MLR Balbc (MMC)/B6 (20 μg dA40(s)/SPG complex i.v.) |
| 4 Allogeneic MLR Balbc (MMC)/B6 (20 μg dA40(s)-siCD40(21 nt)/SPG complex i.v.) |
| 5 Allogeneic MLR Balbc (MMC)/B6 (20 μg dA40(s)-siLuc(21 nt)/SPG complex i.v.) |
| 6 Syngeneic MLR B6 (PBS i.v.)/B6 (PBS i.v.) |

Figure 7:
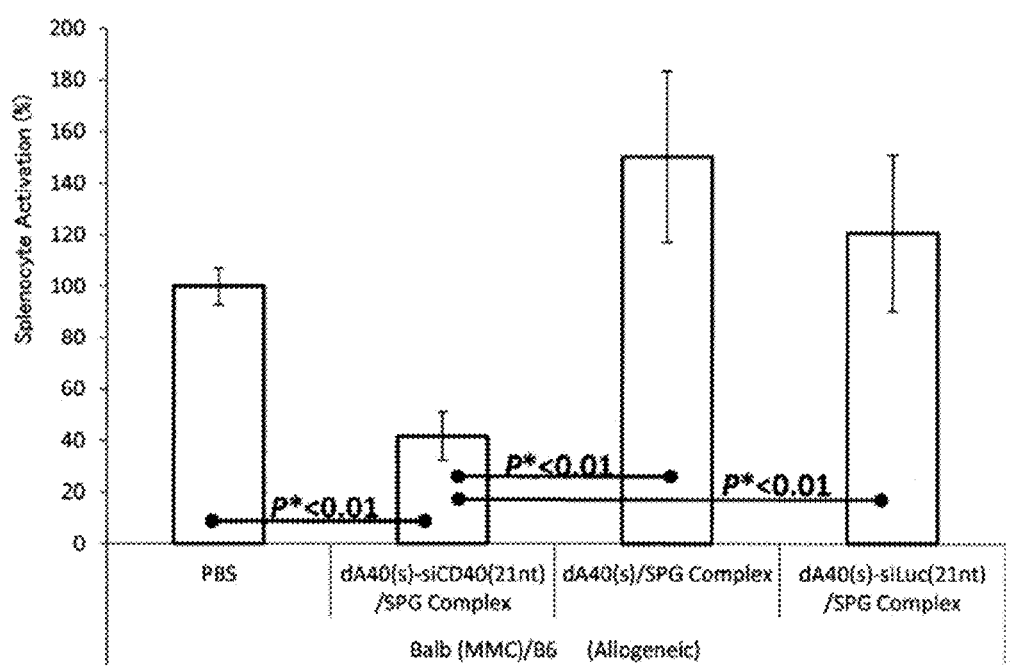
FIG. 7 is a chart showing the results of Example 11 (11-A), or that is, administration of a dA40(s)-siCD40(21 nt)/SPG complex significantly inhibited activation of lymphocytes.

The obtained results are shown in FIG. 7. In FIG. 7, the value (splenocyte activity) obtained by subtracting the numerical value of the syngeneic reaction from the numerical value of the allogeneic reaction of a control (value obtained by subtracting the sample 2 cell count from the sample 6 cell count) is plotted as 100%, and how much the lymphocyte proliferative reaction resulting from the allogeneic reaction was inhibited by the administration of the dA40(s)-siCD40(21 nt)/SPG complex is shown. It is clear from the results that the dA40(s)-siCD40(21 nt)/SPG complex significantly inhibits lymphocyte activation by in vivo administration.

11-B

In this experiment, the behavior of siRNA in a living body was examined by administering a dA40(s)-siCD40(21 nt)/SPG complex into both responder mice and stimulator mice by a caudal vein injection (i.v.), collecting spleen cells after a lapse of 12 hours, and carrying out MLR with stimulator mouse spleen cells. The cell preparation method is as follows.

Spleen cells were collected from mice (stimulators: Balb/c (8 weeks old male, 3 mice) and responders: C57BL/6 (8 weeks old male, 3 mice)). An siRNA/SPG complex was intravenously injected into the stimulator mice and the responder mice 12 hours before collecting spleen cells. Hemolyzing agents (ammonium chloride, potassium) were added to dissolve erythrocytes (5 ml hemolyzing agent, 5 ml RPMI). Cells were suspended in 5 ml of 10% FBS (DS Pharma Biomedical Co., Ltd.)+RPMI ($4 \times 10^5$ cells/wel), and the stimulator spleen cells were treated with mitomycin C (MMC) (25 μg MMC added to final $10^7$ cells). MLR conditions are shown in Table 15.

TABLE 15

| MLR conditions |
| --- |
| Sample |
| 1 Medium |
| 2 Allogeneic MLR Balbc (MMC)/B6 (PBS) |
| 3 Allogeneic MLR Balbc (MMC)/B6 (20 μg dA40(s)-siLuc(21 nt)/SPG complex i.v.) |
| 4 Allogeneic MLR Balbc (MMC)/B6 (20 μg dA40(s)-siCD40(21 nt) and SPG separately present in solution i.v.) |
| 5 Allogeneic MLR Balbc (MMC)/B6 (20 μg dA40(s)-siCD40(21 nt)/SPG complex i.v.) |
| 6 Syngeneic MLR B6 (PBS i.v.)/B6 (PBS i.v.) |

Figure 8:
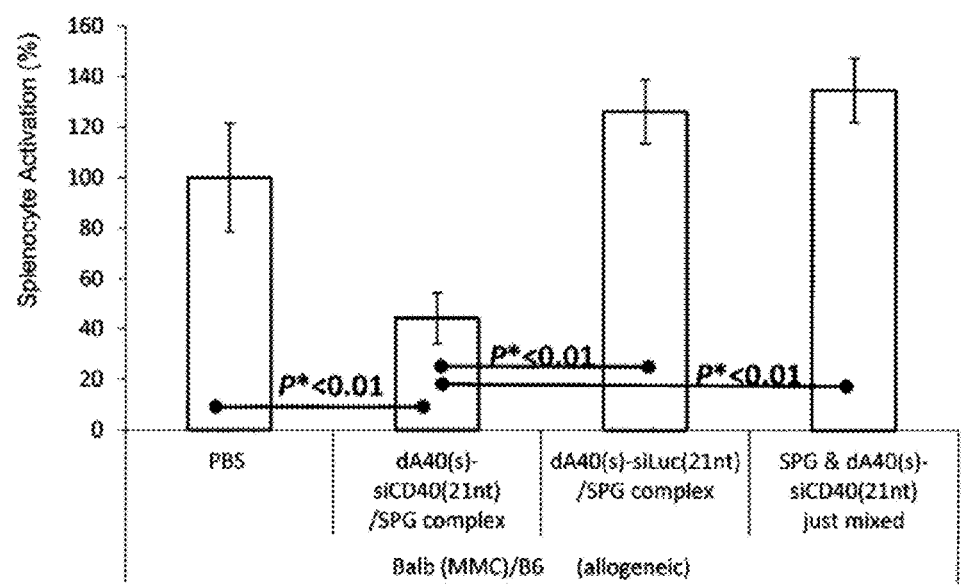
FIG. 8 is a chart showing the results of Example 11 (11-B), or that is, administration of a dA40(s)-siCD40(21 nt)/SPG complex significantly inhibited activation of lymphocytes.

The obtained results are shown in FIG. 8. In FIG. 8, the value (splenocyte activity) obtained by subtracting the numerical value of the syngeneic reaction from the numerical value of the allogeneic reaction of a control (value obtained by subtracting the sample 2 cell count from the sample 6 cell count) is plotted as 100%, and how much the lymphocyte proliferative reaction resulting from the allogeneic reaction was inhibited by the administration of the dA40(s)-siCD40(21 nt)/SPG complex is shown. It was confirmed also from the results that, as with the results of (9-A) above, the dA40(s)-siCD40(21 nt)/SPG complex significantly inhibits lymphocyte activation by in vivo administration.

Example 12

Spleen cells were collected from Balb/c mice. Cells were seeded onto a 24-well plate in an amount of $5 \times 10^6$ cells/well, and an RPMI culture medium containing 10 vol % FBS was added so as to achieve 1 ml/well. A dA40(s)-siCD40(21 nt)/SPG complex (300 ng/well in terms of siRNA) that used SPG with side chain modification by biotin or a PBS-containing control sample as siMock was added to the plate, and cultured in a $CO_2$ incubator (37° C.) overnight. The culture medium was removed by suction, then cells were resuspended in 10 mM Tris-HCl (PH 7.5) containing 100 mM NaCl and 1 mM EDTA and disrupted for 15 seconds by a sonicator, 50 ml of streptavidin-labeled magnetic particles (Roche Applied Science, cat No. 11641778001) were added, and a reaction was carried out at room temperature for 15 minutes while stirring. Centrifugation was carried out to collect a precipitate, the resulting precipitate was resuspended in 100 µl of a sodium dodecyl sulfate (SDS) buffer, subjected to SDS-polyacrylamide electrophoresis, and transferred to a nitrocellulose membrane. Next, detection of TRBP2 was carried out with a mouse anti-TRBP2 antibody and a peroxidase-bound anti-mouse IgG antibody.

As a result, it was found that dA40(s)-siCD40(21 nt) that is in the form of a complex with SPG is in a complex form with TRBP2.

Example 13

The effect of a dA40(s)-siCD40(21 nt)/SPG complex was studied in cardiac allograft by using model mice of heterotopic cardiac transplantation.

More specifically, a dA40(s)-siCD40(21 nt)/SPG complex was administered through the tail vein to donor mice (C57/BL10, male) and recipient mice (CBA, male) at a dose of 2 µg/head. The dosage schedules are as follows. A dose of 2 µg/head at one time was administered to the donor mouse 3 days before (on day −3) and 1 day before (on day −1) cardiac extirpation, and a dose of 2 mg/head at one time was administered to the recipient mouse 3 days before (on day −3) and 1 day before (on day −1) transplantation in the same way. On day 0, the heart was excised from the donor mouse, and the heart was surgically transplanted heterotopically into the recipient mouse. After the transplantation, each dose of 2 µg/head of a dA40(s)-siCD40(21 nt)/SPG complex at one time was further administered through the tail vein to the recipient mouse 1 day (day 1), 3 days (day 3), 5 days (day 5), and 7 days (day 7) after the cardiac transplantation. After the completion of administration, the heartbeat of the transplanted heart of the recipient mouse was observed over time. In addition, as a comparison, a test where a dA40(s)-siGAPDH(glyceraldehyde-3-phosphate dehydrogenase)(21 nt)/SPG complex instead of the dA40(s)-siCD40(21 nt)/SPG complex was administered in the same amount and a test where the dA40(s)-siCD40(21 nt)/SPG complex was not administered were performed in the same manner as above.

Figure 9:
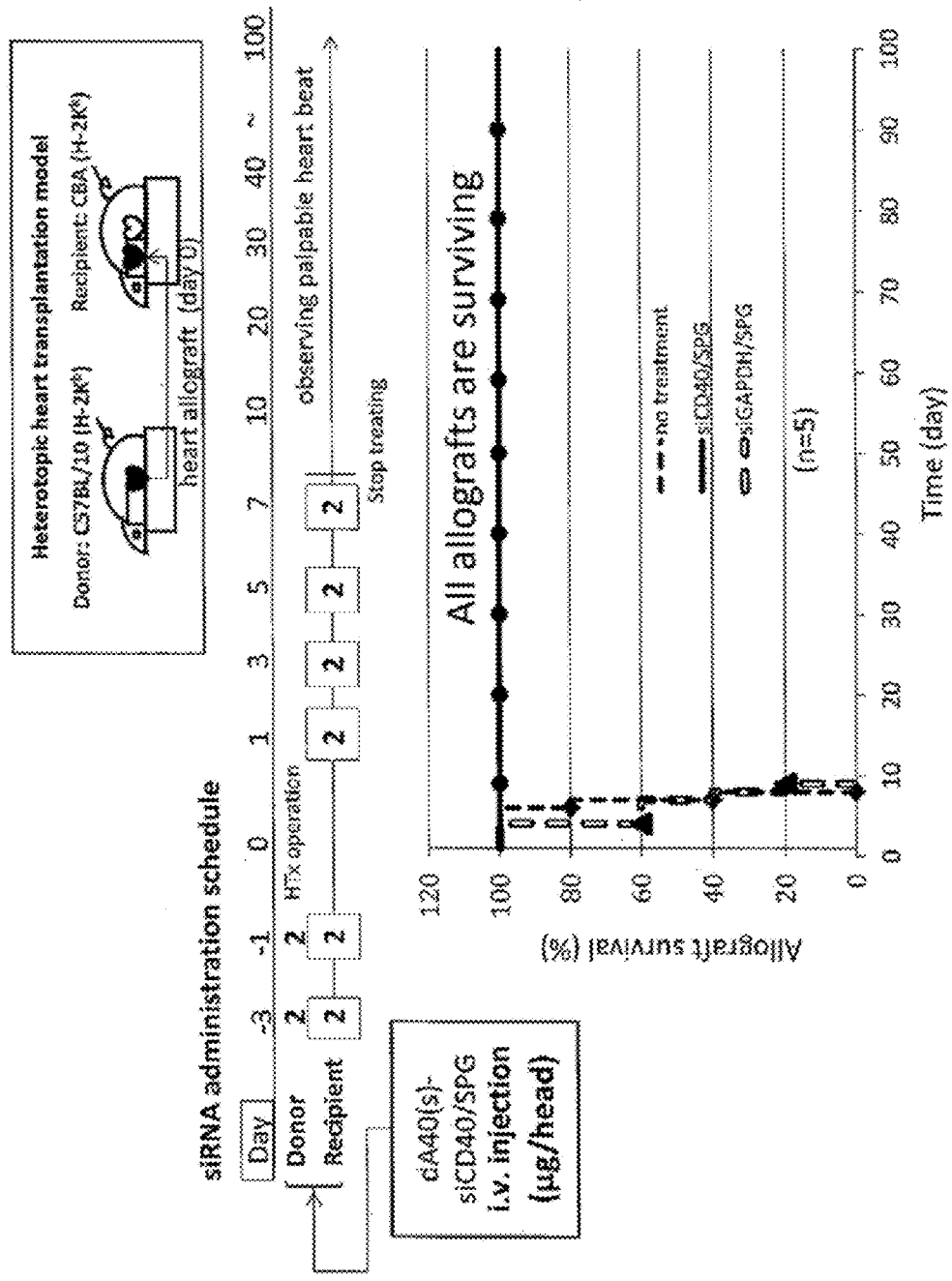
FIG. 9 is a chart showing the results of Example 13, or that is, in a mouse model of heterotopic cardiac transplantation administered with a dA40(s)-siCD40(21 nt)/SPG complex, the heartbeat of the transplanted heart is normal for a long period of time and the survival rate after transplantation is high.

The obtained results are shown in FIG. 9. In FIG. 9, "siCD40/SPG complex" indicates a dA40(s)-siCD40(21 nt)/SPG complex, and "siGAPDH/SPG complex" indicates a dA40(s)-siGAPDH(21 nt)/SPG complex. As can be seen from FIG. 9, when the dA40(s)-siCD40(21 nt)/SPG complex was administered, the beat of the transplanted heart was normal for a long period of time in all the recipient mice after the transplantation, and survival of all recipient mice was confirmed even at 90 days after the transplantation. On the other hand, when the dA40(s)-siGAPDH(21 nt)/SPG complex was administered or nothing was administered, the survival rate of the recipient mice was 0% on day 10 after the transplantation.

Moreover, when the dA40(s)-siCD40(21 nt)/SPG complex was administered to only donor mice (C57/BL10, male) at a dose of 2 µg/head, or administered to only recipient mice (CBA, male) at a dose of 2 µg/head, the beat of the transplanted heart was observed. As a result, the beat of the transplanted heart was observed over a long period of time even in the case where only donor mice or only recipient mice received the administration.

From these results, it is believed that the dA40(s)-siCD40 (21 nt) was effectively introduced into antigen-presenting cells to suppress the expression of CD40 so that the activation of antigen-specific T cells was suppressed.

Note that the nucleotide sequences of siLuc and siCD40 used in Examples 1 to 13 are as shown in Table 16 below.

TABLE 16

| | | | | |
|---|---|---|---|---|
| siLuc (21 nt) sequence (5'→3') | Sense | GGC CUU UCA CUA CUC CUA CGA | SEQ ID NO. 1 |
| | Antisense | GUA GGA GUA GUG AAA GGC CAG | SEQ ID NO. 2 |
| siLuc (27 nt) sequence (5'→3') | Sense | CUG GCC UUU CAC UAC UCC UAC GAG CAC | SEQ ID NO. 3 |
| | Antisense | GUG CUC GUA GGA GUA GUG AAA GGC CAG | SEQ ID NO. 4 |
| siCD40 (21 nt) sequence (5'→3') | Sense | GGA GGG CAC CGC AGA AUC AUU | SEQ ID NO. 5 |
| | Antisense | UGA UUC UGC GGU GCC CUC CUU | SEQ ID NO. 6 |
| siCD40 (27 nt) sequence (5'→3') | Sense | AAG GAG GGC ACC GCA GAA UCA GAC ACU | SEQ ID NO. 7 |
| | Antisense | AGU GUC UGA UUC UGC GGU GCC CUC CUU | SEQ ID NO. 8 |

The invention claimed is:

1. A method for suppressing rejection occurring in transplantation therapy, comprising the step of intravenously administering a nucleic acid-polysaccharide complex of schizophyllan and a polynucleotide containing an siRNA to which polydeoxyadenine is added, against a costimulatory factor, to an animal in need of treatment or prophylaxis of resistance or rejection to a transplanted organ or tissue, wherein the costimulatory factor is Cluster of Differentiation 40 (CD40).

2. The method according to claim 1, wherein the siRNA is a 21mer type, and the polynucleotide contains polydeoxyadenine that has phosphodiester links at least partially phosphorothioated and that is added to a sense strand of the siRNA.

3. The method according to claim 1, wherein at least 50% of the phosphodiester links of the polydeoxyadenine are phosphorothioated.

4. The method according to claim 1, wherein the transplantation therapy is kidney transplantation, heart transplantation, lung transplantation, bone marrow transplantation, skin transplantation, or corneal transplantation.

* * * * *

SEQUENCE LISTING

<160> NUMBER OF SEQ ID NOS: 12

<210> SEQ ID NO 1
<211> LENGTH: 21
<212> TYPE: RNA
<213> ORGANISM: Artificial
<220> FEATURE:
<223> OTHER INFORMATION: Sense strand of siLuc(21nt)

<400> SEQUENCE: 1
ggccuuucac uacuccuacg a                     21

<210> SEQ ID NO 2
<211> LENGTH: 21
<212> TYPE: RNA
<213> ORGANISM: Artificial
<220> FEATURE:
<223> OTHER INFORMATION: Antisense strand of siLuc(21nt)

<400> SEQUENCE: 2
guaggaguag ugaaaggcca g                                              21

<210> SEQ ID NO 3
<211> LENGTH: 27
<212> TYPE: RNA
<213> ORGANISM: Artificial
<220> FEATURE:
<223> OTHER INFORMATION: Sense strand of siLuc(27nt)

<400> SEQUENCE: 3
cuggccuuuc acuacuccua cgagcac                                        27

<210> SEQ ID NO 4
<211> LENGTH: 27
<212> TYPE: RNA
<213> ORGANISM: Artificial
<220> FEATURE:
<223> OTHER INFORMATION: Antisense strand of siLuc(27nt)

<400> SEQUENCE: 4
gugcucguag gaguagugaa aggccag                                        27

<210> SEQ ID NO 5
<211> LENGTH: 21
<212> TYPE: RNA
<213> ORGANISM: Artificial
<220> FEATURE:
<223> OTHER INFORMATION: Sense strand of siCD40(21nt)

<400> SEQUENCE: 5
ggagggcacc gcagaaucau u                                              21

<210> SEQ ID NO 6
<211> LENGTH: 21
<212> TYPE: RNA
<213> ORGANISM: Artificial
<220> FEATURE:
<223> OTHER INFORMATION: Antisense strand of siCD40(21nt)

<400> SEQUENCE: 6 ugauucgcg gugcccuccu u                                               21

<210> SEQ ID NO 7
<211> LENGTH: 27
<212> TYPE: RNA
<213> ORGANISM: Artificial
<220> FEATURE:
<223> OTHER INFORMATION: Sense strand of siCD40(27nt)

<400> SEQUENCE: 7
aaggagggca ccgcagaauc agacacu                                        27

<210> SEQ ID NO 8
<211> LENGTH: 27
<212> TYPE: RNA
<213> ORGANISM: Artificial
<220> FEATURE:

```
<223> OTHER INFORMATION: Antisense strand of siCD40(27nt)

<400> SEQUENCE: 8
agugucugau ucugcgguge ccuccuu                                    27

<210> SEQ ID NO 9
<211> LENGTH: 20
<212> TYPE: DNA
<213> ORGANISM: Artificial
<220> FEATURE:
<223> OTHER INFORMATION: Forward primer for mouse CD40

<400> SEQUENCE: 9
caaggattgc gaggcatgtg                                            20

<210> SEQ ID NO 10
<211> LENGTH: 25
<212> TYPE: DNA
<213> ORGANISM: Artificial
<220> FEATURE:
<223> OTHER INFORMATION: Reverse primer for mouse CD40

<400> SEQUENCE: 10
tgacagacgg tatcagtggt ctcag                                      25

<210> SEQ ID NO 11
<211> LENGTH: 19
<212> TYPE: DNA
<213> ORGANISM: Artificial
<220> FEATURE:
<223> OTHER INFORMATION: Forward primer for mouse beta-actin

<400> SEQUENCE: 11
tggcacccag cacaatgaa                                             19

<210> SEQ ID NO 12
<211> LENGTH: 25
<212> TYPE: DNA
<213> ORGANISM: Artificial
<220> FEATURE:
<223> OTHER INFORMATION: Reverse primer for mouse be-ta-actin

<400> SEQUENCE: 12
ctaagtcata gtccgcctag aagca                                      25
```